(12) United States Patent
Smejkalova et al.

(10) Patent No.: US 9,999,678 B2
(45) Date of Patent: Jun. 19, 2018

(54) $C_6$-$C_{18}$-ACYLATED DERIVATIVE OF HYALURONIC ACID AND METHOD OF PREPARATION THEREOF

(71) Applicant: Contipro Biotech s.r.o., Dolni Dobrouc (CZ)

(72) Inventors: Daniela Smejkalova, Pisek (CZ); Gloria Huerta-Angeles, Ceska Trebova (CZ); Martin Bobek, Prague (CZ); Martina Hermannova, Jacovce (SK); Lucie Vistejnova, Kralovice (CZ); Jaroslav Novotny, Letohrad (CZ); Eva Prikopova, Techonin (CZ); Kristina Nesporova, Brno (CZ); Miroslava Nemcova, Chocen (CZ); Klara Slezingrova, Nekor (CZ); Jaromir Kulhanek, Pardubice (CZ); Dagmar Cozikova, Temice (CZ); Jana Sogorkova, Dobrin (CZ); Jan Kucera, Hradec Kralove (CZ); Pavel Klein, Dolni Dobrouc (CZ); Vladimir Velebny, Zamberk (CZ)

(73) Assignee: Contipro a.s., Dolni Dobrouc (CZ)

( * ) Notice: Subject to any disclaimer, the term of this patent is extended or adjusted under 35 U.S.C. 154(b) by 0 days. days.

(21) Appl. No.: 14/647,626

(22) PCT Filed: Nov. 26, 2013

(86) PCT No.: PCT/CZ2013/000156
§ 371 (c)(1),
(2) Date: May 27, 2015

(87) PCT Pub. No.: WO2014/082609
PCT Pub. Date: Jun. 5, 2014

(65) Prior Publication Data
US 2015/0320873 A1    Nov. 12, 2015

(30) Foreign Application Priority Data
Nov. 27, 2012 (CZ) ..................................... 2012-842

(51) Int. Cl.
*A61K 31/728* (2006.01)
*C08B 37/08* (2006.01)
(Continued)

(52) U.S. Cl.
CPC ........ *A61K 47/4823* (2013.01); *A61K 8/0291* (2013.01); *A61K 8/735* (2013.01);
(Continued)

(58) Field of Classification Search
CPC .. A61K 47/4823; A61K 47/36; A61K 47/488; A61K 8/0291; A61K 8/735;
(Continued)

(56) References Cited

U.S. PATENT DOCUMENTS

| 3,720,662 | A | 3/1973 | Tessler et al. |
| 3,728,223 | A | 4/1973 | Kaneko et al. |

(Continued)

FOREIGN PATENT DOCUMENTS

| CA | 2512730 A1 | 7/2004 |
| CH | 628088 A5 | 2/1982 |

(Continued)

OTHER PUBLICATIONS

Kawaguchi et al., "The relation between the adsorption behavior at the interface and the conformational changes in hyaluronates partially modified with various acyl chains," 1995; Carbohydrate Polymers, 26:149-154.*

(Continued)

*Primary Examiner* — Abigail Vanhorn
(74) *Attorney, Agent, or Firm* — Wood Herron & Evans LLP

(57) ABSTRACT

The invention relates to a method of preparation hydrophobized hyaluronic acid (Formula I) and further to a method of encapsulating biologically active substances into the nanomicelles of hydrophobized hyaluronan serving as carriers of biologically active hydrophobic substances. The hydrophobization of hyaluronan is carried out through an esterification reaction of hyaluronan with long-chain carboxylic acids, the latter being activated by a halogenide derivative of 2,4,6-trichlorobenzoic acid or by another organic chloride. In an aqueous environment, water-soluble hydrophobized derivatives can form nanomicelles in which nonpolar substances can be bound by means of non-covalent physical interactions. The core of a nanomicelle is formed by hydrophobic acyl functional groups while the shell of a nanomicelle is formed by hyaluronic acid. The encapsulation of the substances into nanomicelles can be performed by means of the solvent exchange method or by means of sonication. Hyaluronic nanomicelles support the penetration of bound substances in topical applications and enable the bound substances to be transferred into the individual cells. The nanomicelles obtained from hydrophobized hyaluronan derivatives are usable in cosmetic and pharmaceutical applications.

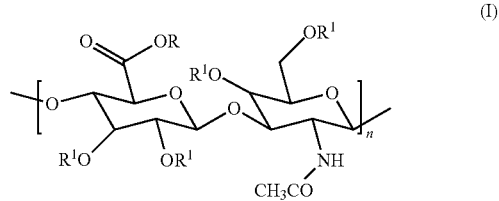

20 Claims, 12 Drawing Sheets

(51) Int. Cl.
| | |
|---|---|
| A61K 47/48 | (2006.01) |
| A61K 31/355 | (2006.01) |
| A61K 31/337 | (2006.01) |
| A61K 31/685 | (2006.01) |
| A61K 31/122 | (2006.01) |
| C08K 3/30 | (2006.01) |
| A61K 8/02 | (2006.01) |
| A61K 8/73 | (2006.01) |
| A61Q 19/00 | (2006.01) |
| A61K 47/36 | (2006.01) |
| A61K 9/107 | (2006.01) |
| A61K 47/69 | (2017.01) |
| A61K 36/00 | (2006.01) |

(52) U.S. Cl.
CPC .......... *A61K 9/1075* (2013.01); *A61K 31/122* (2013.01); *A61K 31/337* (2013.01); *A61K 31/355* (2013.01); *A61K 31/685* (2013.01); *A61K 47/36* (2013.01); *A61K 47/6907* (2017.08); *A61Q 19/00* (2013.01); *C08B 37/0072* (2013.01); *C08K 3/30* (2013.01); *A61K 36/00* (2013.01); *A61K 2800/10* (2013.01); *A61K 2800/413* (2013.01); *A61K 2800/56* (2013.01); *C08K 2003/3045* (2013.01)

(58) Field of Classification Search
CPC .. A61K 9/1075; A61K 31/122; A61K 31/337; A61K 31/355; A61K 31/685; A61K 36/185; A61K 2800/56; A61Q 19/00; C08B 37/0072; C08J 3/24; C08K 3/30
See application file for complete search history.

(56) References Cited

U.S. PATENT DOCUMENTS

| | | | |
|---|---|---|---|
| 4,043,331 | A | 8/1977 | Martin et al. |
| 4,205,025 | A | 5/1980 | Hart et al. |
| 4,258,134 | A | 3/1981 | Yoshida et al. |
| 4,713,448 | A | 12/1987 | Balazs et al. |
| 4,761,401 | A | 8/1988 | Couchman et al. |
| 4,851,521 | A | 7/1989 | Della Valle et al. |
| 4,965,353 | A | 10/1990 | Della Valle et al. |
| 5,455,349 | A | 10/1995 | Grasshoff et al. |
| 5,462,976 | A | 10/1995 | Matsuda et al. |
| 5,520,916 | A | 5/1996 | Dorigatti et al. |
| 5,522,879 | A | 6/1996 | Scopelianos |
| 5,550,225 | A | 8/1996 | Philippe |
| 5,616,568 | A | 4/1997 | Pouyani et al. |
| 5,658,582 | A | 8/1997 | Dorigatti et al. |
| 5,676,964 | A | 10/1997 | Della Valle et al. |
| 5,690,961 | A | 11/1997 | Nguyen |
| 5,824,335 | A | 10/1998 | Dorigatti et al. |
| 5,868,973 | A | 2/1999 | Muller et al. |
| 6,025,444 | A | 2/2000 | Waki et al. |
| 6,075,066 | A | 6/2000 | Matsuda et al. |
| 6,207,134 | B1 | 3/2001 | Fahlvik et al. |
| 6,288,043 | B1 | 9/2001 | Spiro et al. |
| 6,509,039 | B1 | 1/2003 | Nies |
| 6,613,897 | B1 | 9/2003 | Yatsuka et al. |
| 6,632,802 | B2 | 10/2003 | Bellini et al. |
| 6,673,919 | B2 | 1/2004 | Yui et al. |
| 6,683,064 | B2 | 1/2004 | Thompson et al. |
| 6,719,986 | B1 | 4/2004 | Wohlrab et al. |
| 6,902,548 | B1 | 6/2005 | Schuler et al. |
| 6,953,784 | B2 | 10/2005 | Thompson et al. |
| 7,125,860 | B1 | 10/2006 | Renier et al. |
| 7,214,759 | B2 | 5/2007 | Pacetti et al. |
| 7,550,136 | B2 | 6/2009 | Warner et al. |
| 7,680,038 | B1 | 3/2010 | Gourlay |
| 7,951,936 | B2 | 5/2011 | Sato |
| 8,247,546 | B2 | 8/2012 | Stucchi et al. |
| 9,017,725 | B2 * | 4/2015 | Mitra et al. ............... A61K 9/14 424/489 |
| 2002/0026039 | A1 | 2/2002 | Bellini et al. |
| 2002/0076810 | A1 | 6/2002 | Radice et al. |
| 2003/0113354 | A1 * | 6/2003 | Schmid .................... A61K 8/02 424/401 |
| 2003/0163073 | A1 | 8/2003 | Effing et al. |
| 2003/0205839 | A1 | 11/2003 | Bachrach |
| 2004/0101546 | A1 | 5/2004 | Gorman et al. |
| 2004/0192643 | A1 | 9/2004 | Pressato et al. |
| 2005/0112349 | A1 | 5/2005 | Laurencin et al. |
| 2005/0119219 | A1 | 6/2005 | Bellini et al. |
| 2005/0126338 | A1 * | 6/2005 | Yadav .................... B82Y 30/00 75/255 |
| 2005/0266546 | A1 | 12/2005 | Warner et al. |
| 2006/0046590 | A1 | 3/2006 | Chu et al. |
| 2006/0084759 | A1 | 4/2006 | Calabro et al. |
| 2006/0188578 | A1 * | 8/2006 | Fernandez et al. .. A61K 31/728 424/489 |
| 2006/0189516 | A1 | 8/2006 | Yang et al. |
| 2006/0281912 | A1 | 12/2006 | James et al. |
| 2007/0149441 | A1 | 6/2007 | Aeschlimann et al. |
| 2007/0202084 | A1 | 8/2007 | Sadozai et al. |
| 2008/0063617 | A1 | 3/2008 | Abrahams et al. |
| 2008/0071001 | A1 | 3/2008 | Sato |
| 2008/0124395 | A1 | 5/2008 | Chen et al. |
| 2009/0024019 | A1 | 1/2009 | Stein et al. |
| 2009/0180966 | A1 | 7/2009 | Borbely et al. |
| 2009/0252810 | A1 | 10/2009 | Tommeraas et al. |
| 2010/0002155 | A1 | 1/2010 | Yamaguchi et al. |
| 2010/0172892 | A1 | 7/2010 | Uvarkina et al. |
| 2010/0247908 | A1 | 9/2010 | Velev et al. |
| 2010/0310631 | A1 | 12/2010 | Domard et al. |
| 2010/0310853 | A1 | 12/2010 | Schwiegk et al. |
| 2010/0316682 | A1 | 12/2010 | Chen et al. |
| 2011/0020917 | A1 | 1/2011 | Wen et al. |
| 2011/0111012 | A1 | 5/2011 | Pepper et al. |
| 2011/0200676 | A1 | 8/2011 | Lin et al. |
| 2011/0218331 | A1 | 9/2011 | Buffa et al. |
| 2011/0263724 | A1 | 10/2011 | Gurtner et al. |
| 2012/0095205 | A1 | 4/2012 | Buffa et al. |
| 2012/0245323 | A1 | 9/2012 | Buffa et al. |
| 2012/0264913 | A1 | 10/2012 | Buffa et al. |
| 2012/0277416 | A1 | 11/2012 | Carter et al. |
| 2012/0289478 | A1 | 11/2012 | Rovati |
| 2015/0320873 | A1 | 11/2015 | Smejkalova et al. |

FOREIGN PATENT DOCUMENTS

| | | | |
|---|---|---|---|
| CN | 101897976 | A | 12/2010 |
| CN | 101897976 | A * | 12/2010 ............. A61K 47/22 |
| CN | 102154738 | A | 8/2011 |
| CN | 103505736 | A | 1/2014 |
| CZ | 20060605 | A3 | 4/2008 |
| CZ | 20070299 | A3 | 2/2009 |
| CZ | 301899 | B6 | 7/2010 |
| CZ | 302503 | B6 | 6/2011 |
| CZ | 302504 | B6 | 6/2011 |
| CZ | 302856 | B6 | 12/2011 |
| CZ | 302994 | B6 | 2/2012 |
| CZ | 20101001 | A3 | 2/2012 |
| CZ | 20120537 | A3 | 3/2014 |
| CZ | 305153 | B6 | 5/2015 |
| DE | 10331342 | A1 | 2/2005 |
| EP | 0161887 | A2 | 11/1985 |
| EP | 0216453 | A2 | 4/1987 |
| EP | 0763754 | A2 | 3/1997 |
| EP | 0554898 | B1 | 5/1997 |
| EP | 1369441 | A1 | 12/2003 |
| EP | 1454913 | A1 | 9/2004 |
| EP | 1115433 | B1 | 12/2004 |
| EP | 1538166 | A1 | 6/2005 |
| EP | 1217008 | B1 | 3/2006 |
| EP | 1826274 | A1 | 8/2007 |
| EP | 1905456 | A1 | 4/2008 |
| EP | 1607405 | B1 | 5/2011 |
| EP | 2399940 | A2 | 12/2011 |
| EP | 2522337 | A2 | 11/2012 |

(56) References Cited

FOREIGN PATENT DOCUMENTS

| | | | |
|---|---|---|---|
| JP | 62104579 A | 5/1987 | |
| JP | 63044883 A | 11/1988 | |
| JP | H0214019 A | 1/1990 | |
| JP | H0347801 | 2/1991 | |
| JP | 06025306 A | 2/1994 | |
| JP | H0625306 A | 2/1994 | |
| JP | 3308742 B2 | 7/2002 | |
| JP | 2004507586 A | 3/2004 | |
| JP | 2004123785 | 4/2004 | |
| JP | 2007262595 A | 10/2007 | |
| JP | 3975267 B2 | 12/2007 | |
| JP | 2008208480 A | 9/2008 | |
| JP | 2008295885 A | 12/2008 | |
| JP | 2010138276 A | 6/2010 | |
| KR | 20070118730 A | 12/2007 | |
| KR | 20080062092 A | 7/2008 | |
| NL | 9700003 A | 7/1997 | |
| WO | 199311803 A1 | 6/1993 | |
| WO | 199627615 A1 | 9/1996 | |
| WO | 199808876 A1 | 3/1998 | |
| WO | 199901143 A1 | 1/1999 | |
| WO | 199957158 A1 | 11/1999 | |
| WO | 0063470 A1 | 10/2000 | |
| WO | 0134657 A1 | 5/2001 | |
| WO | 0218448 A2 | 3/2002 | |
| WO | 0218450 A1 | 3/2002 | |
| WO | 0232913 A1 | 4/2002 | |
| WO | 0248197 A1 | 6/2002 | |
| WO | 02057210 A1 | 7/2002 | |
| WO | 2005028632 A2 | 3/2005 | |
| WO | WO2005/028632 A2 * | 3/2005 | |
| WO | 2005092390 A2 | 10/2005 | |
| WO | 2005092929 A1 | 10/2005 | |
| WO | 2006010066 A2 | 1/2006 | |
| WO | 2006026104 A2 | 3/2006 | |
| WO | 2006056204 A1 | 6/2006 | |
| WO | WO2006/056204 A1 * | 6/2006 | ............ C08B 37/08 |
| WO | 2007003905 A1 | 1/2007 | |
| WO | 2007006403 A2 | 1/2007 | |
| WO | 2007009728 A2 | 1/2007 | |
| WO | 2007033677 A1 | 3/2007 | |
| WO | WO2007/033677 A1 * | 3/2007 | ............ C08B 37/00 |
| WO | 2007101243 A1 | 9/2007 | |
| WO | 2008014787 A1 | 2/2008 | |
| WO | 2008031525 A1 | 3/2008 | |
| WO | 2008077172 A2 | 7/2008 | |
| WO | 2008115799 A1 | 9/2008 | |
| WO | 2009037566 A2 | 3/2009 | |
| WO | 2009050389 A2 | 4/2009 | |
| WO | 2009108100 A1 | 9/2009 | |
| WO | 2009148405 A1 | 12/2009 | |
| WO | 2010018324 A1 | 2/2010 | |
| WO | 2010051783 A1 | 5/2010 | |
| WO | 2010061005 A1 | 6/2010 | |
| WO | 2010095049 A1 | 8/2010 | |
| WO | 2010095052 A2 | 8/2010 | |
| WO | 2010095056 A2 | 8/2010 | |
| WO | 2010105582 A1 | 9/2010 | |
| WO | 2010130810 A1 | 11/2010 | |
| WO | 2010138074 A1 | 12/2010 | |
| WO | 2011014432 A1 | 2/2011 | |
| WO | 2011028031 A2 | 3/2011 | |
| WO | 2011059325 A2 | 5/2011 | |
| WO | 2011059326 A2 | 5/2011 | |
| WO | 2011069474 A2 | 6/2011 | |
| WO | 2011069475 A2 | 6/2011 | |
| WO | 2012089179 A1 | 7/2012 | |
| WO | 2012146218 A1 | 11/2012 | |
| WO | 2013056312 A1 | 4/2013 | |
| WO | 2013159757 A1 | 10/2013 | |
| WO | 2014023272 A1 | 2/2014 | |
| WO | 2014082608 A1 | 6/2014 | |
| WO | 2014082609 A1 | 6/2014 | |
| WO | 2014082611 A1 | 6/2014 | |

OTHER PUBLICATIONS

Inanaga et al., "A Rapid Esterification by Means of Mixed Anhydride and Its Application to Large-ring Lactonization," 1979; Bulletin of the Chemical Society of Japan, 52(7):1989-1993.*

Eenschooten et al., "Preparation and structural characterisation of novel and versatil amphiphilic octenyl succinic anhydride-modified hyaluronic acid derivatives," 2012; Carbohydrate Polymers, 79:597-605.*

Shen et al., "Synthesis and characterization of low molecular weight hyaluronic acid-based cationic micelles for efficient siRNA delivery," 2009; Carbohydrate Polymers, 77:95-104.*

Liu et al., "Biocompatibility and stability of disulfide-crosslinked hyaluronan films," 2005; Biomaterials, 26:4737-4746.*

Tao et al., "Core cross-linked hyaluronan-styrylpyridinium micelles as a novel carrier for paclitaxel," 2012; Carbohydrate Polymers, 88(1):118-124.*

Wermuth, Drug Discovery Today, 2006, 11(7/8), 348-354.*

Merriam Webster Online Dictionary, obtained online at: http://www.merriam-webster.com/cgi-bin/dictionary?book=Dictionary&va=derivative, downloaded on Jul. 5, 2008.*

Carey et al., Advanced Organic Chemistry Part A: Structure and Mechanisms, Plenum Press, New York and London, pp. 475-479. (Year: 1990).*

Guillaumie, F. et al., Comparative studies of various hyaluronic acids produced by microbial fermentation for potential topical ophthalmic applications. Journal of Biomedical Materials Research Part A; 2009; 1421-1430.

Gupta, P. et al., "Hydrogels: from controlled release to pH-respoonsive drug delivery," Drug Discovery Today (2002) 7 (10):569-579.

Hasegawa, T. et al., "'Click chemistry' on polysaccharides: a convenient, general, and monitorable approach to develop (1-3)-β-D-glucans with various functional appendages," Carbohydrate Research (2006) 341:35-40.

Hewson, W. D. et al., "Oxidation of p-cresol by horseradish peroxidase compound I," J Biol Chem 1976, 251 (19), 6036-42.

Hewson, W. D. et al., "Stoichiometry of the reaction between horseradish peroxidase and p-cresol," J Biol Chem 1976, 251(19), 6043-52.

Higashimura, H. et al., Oxidative Polymerization. John Wiley & Sons, Inc. Olefin Fibers (2002) 10:740-764.

Hocek, M., "Tvorba C-C A C-X Vazeb Cross-Coupling Reakcemi Katalyzovanymi Komplexy Prechodnych Kovu," Chem. Listy (2003) 97:1145-1150.

Hofmann, H. et al., "Conformational Changes of Hyaluronic Acid in Acid Medium," Albrecht Von Graefe's Archive for Clinical and Experimental Opthamology vol. 198, No. 1, 1976, pp. 95-100.

Holten, K.B. et al., "Appropriate Prescribing of Oral Beta-Lactam Antibiotics," American Family Physician (2000) 62 (3):611-620.

Huerta-Angeles, G. et al., "Synthesis of highly substituted amide hyaluronan derivatives with tailored degree of substitution and their crosslinking via click chemistry," Carbohydrate Polymers (2011) 84:1293-1300.

Huh, K.M. et al., "Hydrotropic polymer micelle system for delivery of paclitaxel," Journal of Controlled Release (2005) 101:59-68.

Hynes, W.L. et al., "Hyaluronidases of Gram-positive bacteria," FEMS Microbiology Letters (2000) 183:201-207.

International Preliminary Report on Patentability in International Patent Application No. PCT/CZ2010/000128 dated Feb. 5, 2013.

International Preliminary Report on Patentability in International Patent Application No. PCT/CZ2010/000129, dated Jun. 12, 2012, 5 pgs.

International Search Report (Partial)—Invitation to Pay Fees in International Application No. PCT/CZ2013/000063, 3 pgs.

International Search Report and Written Opinion in International Application No. PCT/CZ2013/000057, dated Jul. 24, 2013, 7 pgs.

International Search Report and Written Opinion in International Patent Application No. PCT/CZ2010/000128, dated Jun. 9, 2011.

International Search Report and Written Opinion in International Patent Application No. PCT/CZ2013/000063, dated Apr. 23, 2015, 16 pgs.

(56) References Cited

OTHER PUBLICATIONS

International Search Report and Written Opinion in International Patent Application No. PCT/CZ2013/000091, dated Oct. 31, 2013, 6 pgs.
International Search Report and Written Opinion in International Patent Application No. PCT/CZ2013/000116, dated Jan. 28, 2014, 8 pgs.
International Search Report in International Patent Application No. PCT/CZ2009/000131, dated Apr. 9, 2010, 3 pgs.
International Search Report in International Patent Application No. PCT/CZ2010/000030, dated Sep. 1, 2010, 3 pgs.
International Search Report in International Patent Application No. PCT/CZ2010/000128, dated Jun. 9, 2011, 3 pages.
International Search Report in International Patent Application No. PCT/CZ2010/000129, dated Jun. 15, 2011, 3 pgs.
International Search Report in International Patent Application No. PCT/CZ2011/000126, dated Apr. 12, 2012, 3 pages.
International Search Report in International Patent Application No. PCT/CZ2012/0000035, dated Aug. 28, 2012, 3 pgs.
International Search Report in International Patent Application No. PCT/CZ2013/000023, dated Aug. 9, 2013, 3 pgs.
International Search Report in International Patent Application No. PCT/CZ2013/000158, dated Mar. 19, 2014, 3 pgs.
International Search Report in International Patent Application No. PCT/CZ2013/000155, dated Feb. 19, 2014, 4 pgs.
International Search Report in International Patent Application No. PCT/CZ2013/000157, dated Mar. 19, 2014, 3 pgs.
Jacoboni, I., "Hyaluronic Acid by Atomic Force Microscopy," Journal of Structural Biology vol. 126, 1999, pp. 52-58.
Jahn, M. et al., "The reaction of hyaluronic acid and its monomers glucuronic acid and N-acetylglucosamine, with reactive oxygen species," Carbohydrate Research, 1999, vol. 321, pp. 228-234.
Japanese Official Action (English language translation) in Japanese Patent Application No. 2012-542355, dated Oct. 17, 2014.
Japanese Official Action (English language translation) in Japanese Patent Application No. 2014-506754, dated Jan. 22, 2015, 2 pgs.
Japanese Official Action (including English language translation) in Japanese Patent Application No. 2012-542356, dated Oct. 3, 2014, 8 pages.
Jia, X.Q. et al., "Synthesis and Characterization of in Situ Cross-Linkable Hyaluronic Acid-Based Hydrogels with Potential Application for Vocal Fold Regeneration," Macromolecules (2004) 37:3239-3248.
Jiang, B. et al., "Study on TEMPO-mediated selective oxidation of hyaluronan and the effects of salt on the reaction kinetics," Carbohydrate Research, Pergamon, GB, vol. 327, No. 4, Aug. 7, 2000, pp. 455-461.
Jin, R.; Hiemstra, C.; Zhong, Z.; Feijen, J., Enzyme-mediated fast in situ formation of hydrogels from dextran-tyramine conjugates. Biomaterials 2007, 28 (18), 2791-2800.
Job, D. et al., "Substituent effect on the oxidation of phenols and aromatic amines by horseradish peroxidase compound I," Eur J Biochem 1976, 66 (3), 607-14.
Jou, Chi-Hsiung et al., "Biocompatibility and Antibacterial Activity of Chitosan and Hyaluronic Acid Immobilized Polyester Fibers," Journal of Applied Polymer Science vol. 104, No. 1, 2007, pp. 220-225.
Juhlin, L., Hyaluronan in skin; Journal of Internal Medicine; 1997; 242; 61-66.
Kalyanaraman, B.; Felix, C. C.; Sealy, R. C., Peroxidatic oxidation of catecholamines. A kinetic electron spin resonance investigation using the spin stabilization approach. Journal of Biological Chemistry 1984, 259 (12), 7584-7589.
Katritzky, A.R. et al., "Cycloaddition Reactions of Heteroaromatic Six-Membered Rings," Chem. Rev. (1989) 89:827-861.
Kawaguchi, Y. et al., "The relation between the adsorption behavior at the interface and the conformational changes in hyaluronates partially modified with various acyl chains," Carbohydrate Polymers (1995) 26:149-154.

Kim, B. et al., "Complexation Phenomena in pH-Responsive Copolymer Networks with Pendent Saccarides," Macromol. (2002) 35:9545-9550.
Korsmeyer, R.W. et al., "Mechanisms of solute release from porous hydrophilic polymers," International Journal of Pharmaceutics (1983) 15:25-35.
Kuo, J.W., "Practical Aspects of Hyaluronan Based Medical Products," 2006, CRC Press, Taylor & Francis Group, pp. 60-61.
Lapcik, L. Jr. et al., Chemicke Listy vol. 85, 1991, pp. 281-298.
Leach, J.B. et al., "Characterization of protein release from photocrosslinkable hyaluronic acid-polyethylene glycol hydrogel tissue engineering scaffolds," Biomaterials (2005) 26:125-135.
Um, I.C. et al., "Electro-Spinning and Electro-Blowing of Hyaluronic Acid," Biomacromolecules (2004) 5:1428-1436.
Uyama, H. et al., Enzymatic Synthesis of Polyphenols. Current Organic Chemistry 2003, 7, 1387-1397.
van Bommel, K.J.C. et al., "Responsive Cyclohexane-Based Low-Molecular-Weight Hydrogelators with Modular Architecture," Angew. Chem. Int. Ed. (2004) 1663-1667.
Veitch, N.C., Horseradish peroxidase: a modem view of a classic enzyme. Phytochemistry 2004, 65 (3), 249-259.
Wang, X. et al., "Formation of water-resistant hyaluronic acid nanofibers by blowing-assisted electro-spinning an dnon-toxic post treatments," Polymer vol. 46, No. 13, 2005, pp. 4853-4867.
Weng, L. et al., "In vitro and in vivo suppression of cellular activity by guanidinoethyl disulfied released from hydrogel microspheres componsed of partially oxidized hyaluronan and gelatin", Biomaterials, Aug. 3, 2008, vol. 29, pp. 4149-4156.
Weng, L. et al., "Self-crosslinkable hydrogels composed of partially oxidized hyaluronan and gelatin: In vitro and in vivo responses", Journal of Biomedical Materials Research Part A, Aug. 9, 2007, pp. 352-365.
Won, K. et al., "Horseradish Peroxidase-Catalyzed Polymerization of Cardanol in the Presence of Redox Mediators," Biomacromolecules (2003) 5(1), 1-4.
Written Opinion in International Patent Application No. PCT/CZ2009/000131, dated Apr. 9, 2010, 3 pgs.
Written Opinion in International Patent Application No. PCT/CZ2010/000030, dated Sep. 1, 2010, 4 pgs.
Written Opinion in International Patent Application No. PCT/CZ2011/000126, dated Apr. 12, 2012, 4 pgs.
Written Opinion in International Patent Application No. PCT/CZ2012/000035, dated Aug. 28, 2012, 4 pgs.
Written Opinion in International Patent Application No. PCT/CZ2013/000023, dated Aug. 9, 2013, 3 pgs.
Written Opinion in International Patent Application No. PCT/CZ2013/000155, dated Feb. 19, 2014, 6 pgs.
Written Opinion in International Patent Application No. PCT/CZ2013/000157, dated Mar. 19, 2014, 6 pgs.
Written Opinion in International Patent Application No. PCT/CZ2013/000158, dated Mar. 19, 2014, 7 pgs.
Xu, Y.-P et al., "Kinetics of phenolic polymerization catalyzed by peroxidase in organic media," Biotechnology and Bioengineering 1995, 47 (1), 117-119.
Yamane, Shintaro et al., "Feasibility of chitosan-based hyaluronic acid hybrid biomaterial for a novel scaffold in cartilage tissue engineering," Biomaterials vol. 26, No. 6, 2005, pp. 611-619.
Yao, F. et al., "A Novel Amphoteric, pH-Sensitive, Biodegradable Poly[chitosan-g-(L-lactic-co-citric) acid] Hydrogel," Journal of Applied Polymer Science (2003) 89:3850-3854.
Yeom, Junseok et al., "Effect of Cross-Linking Reagents for Hyaluronic Acid Hydrogel Dermal Fillers on Tissue Augmentation and Regeneration," Bioconjugate Chemistry (2010) 21(2)240-247.
Zhong, S.P. et al., "Biodegradation of hyaluronic acid derivatives by hyalurondiase," Biomaterials vol. 15, No. 5, 1994, pp. 359-365.
Leach, J.B. et al., "Photocrosslinked Hyaluronic Acid Hydrogels: Natural, Biodegradable Tissue Engineering Scaffolds," Biotechnol Bioeng. (2003) 82:578-589.
Lee, F. et al., "An injectable enzymatically crosslinked hyaluronic acid-tyramine hydrogel system with independent tuning of mechanical strength and gelation rate," Soft Matter 2008, 4, 880-887.

(56) References Cited

OTHER PUBLICATIONS

Lee, K.Y. et al., "Electrospinning of polysaccharides for regenerative medicine," Advanced Drug Delivery Reviews (2009) 61:1020-1032.
Lee, S.A. et al., Spectroscopic studies of the physical properties of hyaluronate films: the origin of the phase transition; Carbohydrate Polymers; 1995; 28; 61-67.
Linhardt, R.J. et al., "Polysaccharide lyases," Applied Biochemistry and Biotechnology (1986) 12:135-176.
Linhartova, B., Nanovlakna na bazi hyaluronanu, Bakalarska prace, Vysoke uceni technicke v Brne, 2008 (English language Abstract on p. 3).
Liu, Yanchun et al., "Biocompatibility and stability of disulfide-crosslinked hyaluronan films," Biomaterials vol. 26, No. 23, 2005, pp. 4737-4746.
Luo, Yanfeng et al., "Novel amphoteric pH-sensitive hydrogels derived from ethylenediaminetetraacetic dianhydride, butanediamine and amino-terminated poly(ethylene glycol): Design, synthesis and swelling behavior," European Polymer Journal (2011) 47:40-47.
Malkoch, M. et al., "Synthesis of well-defined hydrogel networks using Click chemistry," Chem. Commun. (2006) 2774-2776.
Matsushima, R. et al., "Photoreactions of Alkylated 2-Pyridones," J. Chem. Soc. Perkin Trans. 2 (1985) 1445-1448.
McIntyre, J.E., "The Chemistry of Fibres," Studies in Chemistry No. 6, 1971, p. 15.
McTaggart, L.E. et al., "Assessment of polysaccharide gels as drug delivery vehicles," Int. J. Pharm. 1993, vol. 100, pp. 199-206.
Miller, R.J. et al., Chemistry and Biology of Hyaluronan : Medicinal Uses of Modified Hyaluronate. Elsevier Ltd. 2004. 505-528.
Nevell, T.P. et al., "Cellulose Chemistry and its Applications," 1985, John Wiley & Sons, pp. 455-479.
Oh, E.J. et al., "Target specific and long-acting delivery of protein, peptide, and nukleotide therapeutics using hyaluronic acid derivatives," J. Controlled Release vol. 141, 2010, pp. 2-12.
Pal, K. et al., "Biopolymers in Controlled-Release Delivery Systems," Modern Biopolymer Science (2009) 519-557.
Park, Y.D. et al., Photopolymerized hyaluronic acid-based hydrogels and interpenetrating networks, Biomaterials (2003) 24:893-900.
Patel, P. K.; Monda!, M. S.; Modi, S.; Behere, D. V., Kinetic studies on the oxidation of phenols by the horseradish peroxidase compound II. Biochim Biophys Acta 1997, 1339 (1), 79-87.
Piluso, S. et al., "Hyaluronic acid-based hydrogels crosslinked by copper-catalyzed azide-alkyne cycloaddition with tailorable mechanical properties," International Journal of Artificial Organs (2011) 34:192-197, Abstract.
Prestwich, G.D., "Hyaluronic acid-based clinical biomaterials derived for cell and molecule delivery in regenerative medicine," Journal of Controlled Release (2011) 155:193-199.
Prestwich, G.D., internet article "Biomaterials from Chemically-Modified Hyaluronan", Feb. 26, 2001, 17 pages.
Qiu, Y. et al., "Environment-sensitive hydrogels for drug delivery," Advanced Drug Delivery Reviews (2001) 53:321-339.
Rao, K.V.R. et al., "Influence of Molecular Size and Water Solubility of the Solute on its Release from Swelling and Erosion Controlled Polymeric Matrices," Journal of Controlled Release (1990) 12:133-141.
Remy, H., Anorganicka chemie II., Sntl Praha 1971, pp. 306-321.
Ritger, P.L. et al., "A Simple Equation for Description fo Solute Release I. Fickian and Non-Fickian Release from Non-Swellable Devices in the Form of Slabs, Spheres, Cylinders or Discs," Journal of Controlled Release (1987) 5:23-36.
Ritger, P.L. et al., "A Simple Equation for Description fo Solute Release II. Fickian and Anomalous Release from Swellable Devices," Journal of Controlled Release (1987) 5:37-42.
Rostovtsev, V.V. et al., "A Stepwise Huisgen Cycloaddition Process: Copper(I)-Catalyzed Regioselective 'Ligation' of Azides and Terminal Alkynes," Angew. Chem. Int. Ed. (2002) 41(14):2596-2599.

Rupprecht, A., Wet Spinning of Hyaluronic Acid. Preparation of Oriented Samples; Acta Chemica Scandinavica; 1979; 33; 779-780.
Schante, C.E. et al., "Chemical modifications of hyaluronic acid for the synthesis of derivatives for a broad range of biomedical applications," Carbohydrate Polymers (2011) 85:469-489.
Scott, J.E. et al., "Periodate Oxidation of Acid Polysaccharides", Histochemie, Apr. 26, 1969, vol. 19, pp. 155-161.
Scott, J.E. et al., "Secondary and tertiary structures of hyaluronan in aqueous solution, investigated by rotary shadowing—electron microscopy and computer simulation," J. Biochem vol. 274, 1991, pp. 699-705.
Sedova, P. et al., "Preparation of hyaluronan polyaldehyde—a precursor of biopolymer conjugates," Carbohydrate Research (2013) 371:8-15.
Seidlits, S.K. et al., "The effects of hyaluronic acid hydrogels with tunable mechanical properties on neural progenitor cell differentiation" Biomaterials (2010) 31:3930-3940.
Shang, J. et al., "Chitosan-based electroactive hydrogel," Polymer (2008) 49:5520-5525.
Sheehan, J.K. et al., X-ray diffraction studies on the connective tissue polysaccharides; J. Mol. Biol. 1975; 91; 153-163.
Shimizu, M. et al., "Studies on hyaluronidase, chondroitin sulphatase, proteinase and phospholipase secreted by Candida species," Mycoses (1996) 39:161-167.
Shutava, T. et al., "Microcapsule modification with peroxidase-catalyzed phenol polymerization," Biomacromolecules 2004, 5 (3), 914-21.
Sieburth, S.M. et al., "Fusicoccin Ring System by [4+4] Cycloaddition. 2. A Model Study," Tetrahedron Letters (1999) 40:4007-4010.
Sieburth, S.M. et al., "The [4+4] Cycloaddition and its Strategic Application in Natural Product Synthesis," Tetrahedron (1996) 52(18):6251-6282.
Slaughter, B. V.; Khurshid, S. S.; Fisher, O. Z.; Khademhosseini, A.; Peppas, N. A., Hydrogels in Regenerative Medicine. Advanced Materials 2009, 21 (32-33), 3307-3329.
Slezingrova, K. et al., "Synteza a charakterizace palmitoyl hyaluronanu," Chemicke Listy (2012) 106:554.
Smeds, K.A. et al., "Photocrosslinkable polysaccharides for in situ hydrogel formation," J. Biomed. Mater. Res. (2001) 54:115-121.
Staskus, P.W. et al., "Double-Stranded Structure for Hyaluronic Acid in Ethanol-Aqueous Solution As Revealed by Circular Dichroism of Oligomers," Biochemistry vol. 27, No. 5, 1988, pp. 1528-1534.
Svanovsky, E. et al., "The effect of molecular weight on the biodistribution of hyaluronic acid radiolabeled with 111-In after intravenous administration to rats," Eur. J. Drug Metab. Ph. 2008, vol. 33, No. 3, pp. 149-157.
Tan, H.; Chu, C. R.; Payne, K. A.; Marra, K. G., Injectable in situ forming biodegradable chitosan-hyaluronic acid based hydrogels for cartilage tissue engineering. Biomaterials 2009, 30 (13), 2499-2506.
Tankam, P.F. et al., "Alkynyl polysaccharides: synthesis of propargyl potato starch followed by subsequent derivatizations," Carbohydrate Research (2007) 342:2049-2060.
Testa, G. et al., "Influence of dialkyne structure on the properties of new click-gels based on hyaluronic acid," International Journal of Pharmaceutics (2009) 378:86-92.
Tonelli, A. E., Effects of crosslink density and length on the number of intramolecular crosslinks (defects) introduced into a rubbery network. Polymer 1974, 15 (4), 194-196.
Tornoe, C. et al., "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem. (2002) 67:3057-3064.
Aldrich, Chem Files Synthetic Methods Oxidation (English translation), May 2005, vol. 5, No. 1 pp. 1-11.
Author unknown, Encyclopedia of Cellulose (English translation), Asakura Publishing Co., Ltd., pp. 155-156 (Nov. 10, 2000).
Office Action in U.S. Appl. No. 13/512,484, dated Oct. 1, 2015, 8 pgs.
Office Action in U.S. Appl. No. 13/512,484, dated Sep. 11, 2014, 8 pgs.

(56) References Cited

OTHER PUBLICATIONS

Office Action in U.S. Appl. No. 13/514,759, dated Jul. 30, 2015, 12 pgs.
Office Action in U.S. Appl. No. 13/514,759, dated Sep. 24, 2014, 10 pgs.
Office Action in U.S. Appl. No. 13/977,181, dated Jan. 22, 2016, 8 pgs.
Office Action in U.S. Appl. No. 14/113,527, dated Feb. 12, 2016, 11 pgs.
Boyer, I. J. (1989). Toxicity of dibutyltin, tributyltin and other organotin compounds to humans and to experimental animals. Toxicology, 55(3), 253-298.
Eenschooten, C. et al., Preparation and structural characterisation of novel and versatile amphiphilic octenyl succinic anhydride-modified hyaluronic acid derivatives, Carbohydrate Polym Ers, vol. 79, No. 3, 2010, pp. 597-605.
Gong, J. et al., (2012). Polymeric micelles drug delivery system in oncology. Journal of Controlled Release, 159(3), 312-323.
Inanaga, J. et al., A Rapid Esterification by Means of Mixed Anhydride and Its Application to Large-ring Lactonization, Bulletin of the Chemical Society of Japan, vol. 52, No. 7, 1979, pp. 1989-1993.
Kedar, U. et al., Advances in polymeric micelles for drug delivery and tumor targeting, Nanomedicine Nanotechnology, Biology and Medicine, vol. 6, No. 6, 2010, pp. 714-729.
Kim, T. G., Lee, H., Jang, Y., & Park, T. G. (2009). Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel. Biomacromolecules, 10(6), 1532-1539.
Li, J., Huo, M., Wang, J., Zhou, J., Mohammad, J. M., Zhang, Y., Zhu. Q., Waddad, A. Y., & Zhang, Q. (2012). Redox-sensitive micelles self-assembled from amphiphilic hyaluronic acid-deoxycholic acid conjugates for targeted intracellular delivery of paclitaxel. Biomaterials, 33(7), 2310-2320.
Liu, Y. et al., Dual targeting folate-conjugated hyaluronic acid polymeric micelles for paclitaxel delivery, International Journal of Pharmaceutics, vol. 421, No. 1, 2011, pp. 160-169.
Mayol, L. et al., Amphiphilic hyaluronic acid derivatives toward the design of micelles for the sustained delivery of hydrophobic drugs, Carbohydrate Polymers, vol. 102, Feb. 1, 2014, pp. 110-116.
Mazzone, S. B., Mori, N., Bunnan, M., Palovich, M., Belmonte, K. E.. & Canning, B. J. (2006). Fluorescent styryl dyes FM 1-43 and FM2-10 are muscarinic receptor antagonists: intravital visualization of receptor occupancy. The Journal of Physiology, 575(1), 23-35.
Shen, Y. et al., Synthesis and characterization of low molecular weight hyaluronic acid-based cationic micelles for efficient siRNA delivery, Carbohydrate Polymers, vol. 77, No. 1, 2009, pp. 95-104.
Smejkalova, D., et al., (2012). Structural and conformational differences of acylated hyaluronan modified in protic and aprotic solvent system. Carbohydrate Polymers, 87(2), 1460-1466.
Tao, Y., Xu. J., Chen, M.. Bai, H., & Liu, X. Core cross-linked hyaluronan• styrylpyridinium micelles as a novel carrier for paclitaxel. (2012). Carbohydrate Polymers, 88(1), 118-124.
Til, H. P., Falke, H. E., Prinsen, M. K., & Willems, M. I. (1997). Acute and Subacute Toxicity of Tyramine, Spermidine, Spermine, Putrescine and Cadaverine in Rats. Food and Chemical Toxicology, 35(3-4), 337-348.
Wang, J., Mongayt, D., & Torchilin, V. P. (2005). Polymeric Micelles for Delivery of Poorly Soluble Drugs: Preparation and Anticancer Activity in Vitro of Paclitaxel Incorporated into Mixed Micelles Based on Polyethylene Glycol)-Lipid Conjugate and Positively Charged Lipids. Journal of Drug Targeting, 13(1), 73-80.
Akkara, J. A. et al., "Synthesis and characterization of polymers produced by horseradish peroxidase in dioxane," Journal of Polymer Science Part A: Polymer Chemistry 1991, 29 (11), 1561-1574.
Aldrich, Chem Files Synthetic Methods Oxidation, May 2005, vol. 5, No. 1 pp. 1-11.
Angelin, M. et al., "Direct, Mild, and Selective Synthesis of Unprotected Dialdo-Glycosides", European Journal of Organic Chemistry, Jan. 1, 2006, pp. 4323-4326.
Armstrong, D.C. et al., "Culture Conditions Affect the Molecular Weight Properties of Hyaluronic Acid Produced by *Streptococcus zooepidemicus*," Appl. Environ. Microbiol. (1997) 63(7):2759-2764.
Atkins, E.D.T. et al., "The Conformation of the Mucopolysaccharides," J. Biochem vol. 128, 1972, pp. 1255-1263.
Atkins, E.D.T. et al., "The Molecular Structure of Hyaluronic Acid," Biochemical Journal vol. 125, No. 4, 1971, p. 92.
Author unknown, "Readily Accessible 12-l-51 Oxidant for the Conversion of Primary and Secondary Alcohols to Aldehydes and Ketones," Journal of Organic Chemistry (1983) 84:4155-4156 (English language on pp. 2-3 of document).
Author unknown, Encyclopedia of Cellulose, Asakura Publishing Co., Ltd., pp. 155-156 (Nov. 10, 2000).
Bakke, M. et al., "Identification, characterization, and molecular cloning of a novel hyaluronidase, a member of glycosyl hydrolase family 16, from *Penicillium* spp.," FEBS Letters (2011) 585(1):115-120.
Banerji, S. et al., "Structures of the Cd44-hyaluronan complex provide insight into a fundamental carboxyhydrate-protein interaction," Nature structural and molecular biology (2007) 14:234-239.
Benedetti, L. et al., "Biocompatibility and biodegradation of different hyaluronan derivatives (Hyaff) implanted-in rats," Biomaterials 1993, 14 (15), 1154-1160.
Bezakova, Z. et al., "Effect of microwave irradiation on the molecular and structural properties of hyaluronan," Carbohydrate Polymers, vol. 73, No. 4, 2008, pp. 640-646.
Burdick, J.A. et al., "Controlled Degradation and Mechanical Behavior of Photopolymerized Hyaluronic Acid Networks," Biomacromolecules (2005) 6:386-391.
Burdick, J.A. et al., "Hyaluronic Acid Hydrogels for Biomedical Applications," Adv. Mater. (2011) 23:H41-H56.
Burke, J., Solubility Parameters: Theory and Application, The Book and Paper Group Annual, vol. Three, 1984, 62 pgs.
Burner, U. et al., Transient-state and steady-state kinetics of the oxidation of aliphatic and aromatic thiols by horseradish peroxidase, FEES Letters (1997) 411(2-3), 269-274.
Chen, L. et al., "Synthesis and pH sensitivity of carboxyymethyl chitosan-based polyampholyte hydrogel for protein carrier matrices," Biomaterials (2004) 25:3725-3732.
Cornwell, M.J. et al., "A one-step synthesis of cyclodextrin monoaldehydes," Tetrahedron Letters, vol. 36, No. 46, Nov. 13, 1995, pp. 8371-8374.
Crescenzi, V. et al., "Novel Hydrogels via Click Chemistry: Synthesis and Potential Biomedical Applications," Biomacromolecules (2007) 8:1844-1850.
Czech Official Action in Czech Patent Application No. PV 2008-705 dated Oct. 23, 2009, 2 pgs.
Czech Official Action in Czech Patent Application No. PV 2009-835, dated Aug. 2010, 2 pgs.
Czech Official Action in Czech Patent Application No. PV 2009-836, dated Aug. 6, 2010, 2 pages.
Czech Search Report in Czech Patent Application No. PV 2010-1001, dated Sep. 27, 2011, 1 pg.
Czech Search Report in Czech Patent Application No. PV 2011-241, dated Nov. 30, 2011, 1 pg.
Czech Search Report in Czech Patent Application No. PV 2012-136, dated Sep. 18, 2012, 3 pgs.
Czech Search Report in Czech Patent Application No. PV 2012-282, dated Jan. 30, 2013, 1 pg.
Czech Search Report in Czech Patent Application No. PV 2012-306, dated Feb. 11, 2013, 1 pg.
Czech Search Report in Czech Patent Application No. PV 2012-664, dated May 24, 2013, 3 pgs.
Czech Search Report in Czech Patent Application No. PV 2012-842, dated Aug. 19, 2013, 3 pgs.
Czech Search Report in Czech Patent Application No. PV 2012-843, dated Aug. 20, 2013, 1 pg.

(56) References Cited

OTHER PUBLICATIONS

Darr, A. et al., "Synthesis and characterization of tyramine-based hyaluronan hydrogels," Journal of Materials Science: Materials in Medicine (2009) 20(1), 33-44.
Dilling, W.L. et al., "Organic Photochemistry. XII. The Photodimerization and Photoisomerization of 2-Pyridone and Its Monochloro Derivatives," Mol. Photochem. (1973) 5(4):371-409.
Ding, B. et al., "TEMPO-mediated selective oxidation of substituted polysaccharides—an efficient approach for the determination of the degree of substitution at C-6", Carbohydrate Research, vol. 343, No. 18, Dec. 8, 2008, pp. 3112-3116.
Donati, A. et al., "Solution Structure of Hyaluronic Acid Oligomers by Experimental and Theoretical NMR, and Molecular Dynamics Simulation," Biopolymers vol. 59, 2001, pp. 434-445.
Dumitriu, S., "Characterization and Properties of Hyaluronic Acid (Hyaluronan)," by M. Milas et al., Chap. 22 of Polysaccharides: Structural Diversity and Functional Versatility, 1998, Marcel Dekker Inc., pp. 535-549.
Dunford, H. B. et al., "Kinetics of the oxidation of p-aminobenzoic acid catalyzed by horseradish peroxidase compounds I and II," J Biol Chem 1975, 250(8), 2920-32.
El-Sherbiny, I.M. et al., "Poly(ethylene glycol)-carboxymethyl chitosan-based pH-responsive hydrogels: photo-induced synthesis, characterization, swelling, and in vitro evaluation as potential drug carriers," Carbohydrate Research (2010) 345:2004-2012.
Elander, R.P., "Industrial production of β-lactam antibiotics," Applied Microbiology and Biotechnology (2003) 61:385-392.
European First Official Action in European Patent Application No. 10812840.6-1306, dated Jul. 2, 2013, 10 pages.
European Second Official Action in European Patent Application No. 10812840.6-1306, dated Sep. 24, 2014.
Feng, Qian et al., "Self-Assembly Behaviour of Hyaluronic Acid on Mica by Atomic Force Microscopy," vol. 20, No. 1, 2004, pp. 146-148 and 152 (English language Abstract p. 152).
Ferrero, C. et al., "Fronts movement as a useful tool for hydrophilic matrix release mechanism elucidation," International Journal of Pharmaceutics (2000) 202:21-28.
Ferruti, P. et al., "Novel Poly(amido-amine)-Based Hydrogels as Scaffolds for Tissue Engineering," Macromol. Biosci. (2005) 5:613-622.
Funakoshi, T. et al., "Novel chitosan-based hyaluronan hybrid polymer fibers as a scaffold in ligament tissue engineering," Journal of Biomedical Materials Reasearch, Part A, vol. 74A, No. 3, 2005, pp. 338-346.
Ghan, R. et al., "Enzyme-Catalyzed Polymerization of Phenols within Polyelectrolyte Microcapsules," Macromolecules (2004) 37(12), 4519-4524.
Gibby, W.A., "Cross-Linked DTPA Polysaccharides for Magnetic Resonance Imaging, Synthesis and Relaxation Properties," Invest. Radiol. 1989, vol. 24, pp. 302-309.
Gilabert, M. A. et al., "Differential substrate behaviour of phenol and aniline derivatives during oxidation by horseradish peroxidase: kinetic evidence for a two-step mechanism," Biochim Biophys Acta 2004, 1699 (1-2), 235-43.
Gilabert, M. A. et al., "Kinetic characterization of phenol and aniline derivates as substrates of peroxidase," Biol Chem 2004, 385 (9), 795-800.
Gilabert, M. A. et al., "Stereospecificity of horseradish peroxidase," Biol Chem 2004, 385 (12), 1177-84.
Buffa, R. et al., "Branched hyaluronic acid, synthesis, analysis and biological properties," Journal of Tissue Engineering and Regenerative Medicine (2014) 8(1):321.
Buffa, R. et al., "New method of immobilization of hyaluronic acid oligomers," Journal of Tissue Engineering and Regenerative Medicine (2014) 8(1):321-322.
Duncan, R. et al., "Nanomedicine(s) under the Microscope," Molecular Pharmaceutics (2011) 8(6):2101-2141.
El-Dakdouki, M.H. et al., "Development of drug loaded nanoparticles for tumor targeting. Part 1: synthesis, characterization, and biological evaluation in 2D cell cultures," Nanoscale (2013) 5(9):3895-3903.
El-Dakdouki, M.H. et al., "Development of Multifunctional Hyaluronan-Coated Nanoparticles for Imaging and Drug Delivery to Cancer Cells," Biomacromolecules (2012) 13(4):1144-1151.
Fleige, E. et al., "Stimuli-responsive polymeric nanocarriers for the controlled transport of active compounds: Concepts and applications," Advanced Drug Delivery Reviews (2012) 64(9):866-884.
Godula, K. et al., "Synthesis of Glycopolymers for Microarray Applications via Ligation of Reducing Sugars to a Poly (acryloyl hydrazide) Scaffold," J. Am. Chem. Soc. (2010) 132:9963-9965.
Huang, G. et al., "Superparamagnetic Iron Oxide Nanoparticles: Amplifying ROS Stress to Improve Anticancer Drug Efficacy.," Theranostics (2013) 3(2):116-126.
International Search Report in International Patent Application No. PCT/CZ2014/000138, dated May 4, 2015, 4 pgs.
International Search Report in International Patent Application No. PCT/CZ2015/000018, dated Jul. 22, 2015, 5 pgs.
International Search Report in International Patent Application No. PCT/CZ2015/000068, dated Jan. 8, 2016, 4 pgs.
Kumar, A. et al., "Development of hyaluronic acid-Fe2O3 hybrid magnetic nanoparticles for targeted delivery of peptides," Nanomedicine: Nanotechnology, Biology and Medicine, Elsevier, NL (2007) 3(2)132-137.
Laurent, S. et al., "Magnetic fluid hyperthennia: Focus on superparamagnetic iron oxide nanoparticles," Advances in Colloid and Interface Science (2011) 166:8-23.
Lee, Dong-Eun et al., "Amphiphilic hyaluronic acid-based nanoparticles for tumor-specific optical/MR dual imaging," Journal of Materials Chemistry (2012) 22(1)10444-10447.
Lee, F. et al., "An injectable hyaluronic acid-tyramine hydrogel system for protein delivery," Journal of Controlled Release (2009) 134:186-193.
Lee, Yuhan et al., "Bioinspired Surface Immobilization of Hyaluronic Acid on Monodisperse Magnetite Nanocrystals for Targeted Cancer Imaging," Advanced Materials (2008) 20:4154-4157.
Li, J. et al., "Electrospinning of Hyaluronic Acid (HA) and HA/Gelatin Blends," Macromolecular Rapid Communications (2006) 27:114-120.
Li, M. et al., Comparison of Two Ultrasmall Superparamagnetic Iron Oxides on Cytotoxicity and MR Imaging of Tumors, Theranostics (2012) 2(1):76-85.
Maeda, H., "The Enhanced Permeability and Retention (EPR) Effect in Tumor Vasculature: The Key Role of Tumor-Selective Macromolecular Drug Targeting," Advances in Enzyme Regulation (2001) 41(1):189-207.
Marega, R. et al., "Hyaluronan-Carbon Nanotube Derivatives: Synthesis, Conjugation with Model Drugs, and DOSY NMR Characterization," Eur. J. Org. Chem. (2011) 28:5617-5625.
Office Action in U.S. Appl. No. 13/512,484, dated May 11, 2016, 8 pgs.
Office Action in U.S. Appl. No. 14/113,527, dated Sep. 8, 2016, 10 pgs.
Office Action in U.S. Appl. No. 14/420,012, dated Jun. 16, 2016, 6 pgs.
Office Action in U.S. Appl. No. 14/430,731, dated May 19, 2016, 12 pgs.
Office Action in U.S. Appl. No. 14/647,185, dated Sep. 28, 2016, 5 pgs.
Ruoslahti, E. et al., "Targeting of drugs and nanoparticles to tumors," The Journal of Cell Biology (2010) 188 (6):759-768.
Shen, Yi et al., "Synthesis, Characterization, Antibacterial and Antifungal Evaluation of Novel Monosaccharide Esters," Molecules (2012) 17(7):8661-8673.
Thakar, D. et al., "A quartz crystal microbalance method to study the terminal functionalization of glycosaminoglycans," Chemical Communications (2014) 50(96):15148-15151.
Wondraczek, H. et al., "Synthesis of highly functionalized dextran alkyl carbonates showing nanosphere formation," Carbohydrate Polymers (2011) 83:1112-1118.

(56) References Cited

OTHER PUBLICATIONS

Written Opinion in International Patent Application No. PCT/CZ2014/000138, dated May 4, 2015, 5 pgs.
Written Opinion in International Patent Application No. PCT/CZ2015/000018, dated Jul. 22, 2015, 8 pgs.
Written Opinion in International Patent Application No. PCT/CZ2015/000068, dated Jan. 8, 2016, 6 pgs.
Zeng, J. et al., "Photo-Induced Solid-State Crosslinking of Electrspun Poly(vinyl alcohol) Fibers," Macromolecular Rapid Communications (2005) 26:1557-1562.
Office Action in U.S. Appl. No. 14/395,575, dated Jul. 6, 2017, 9 pgs.
Office Action in U.S. Appl. No. 14/647,649, dated May 31, 2017, 11 pgs.
Office Action in U.S. Appl. No. 15/322,776, dated Jul. 14, 2017, 11 pgs.
International Search Report in International Patent Application No. PCT/CZ2016/000027, dated Jun. 27, 2016, 3 pgs.
Office Action in U.S. Appl. No. 15/322,776, dated Sep. 12, 2017, 23 pgs.
Written Opinion in International Patent Application No. PCT/CZ2016/000027, dated Jun. 27, 2016, 6 pgs.
Office Action in U.S. Appl. No. 15/038,078, dated Nov. 3, 2017, 10 pgs.

\* cited by examiner

$C_6$-$C_{18}$-ACYLATED DERIVATIVE OF HYALURONIC ACID AND METHOD OF PREPARATION THEREOF $C_6$-$C_{18}$-acylated derivative of hyaluronic acid, method of preparation thereof, nanomicellar composition on its basis, method of preparation thereof and method of preparation stabilized nanomicellar composition, and use thereof

FIELD OF THE INVENTION

The invention relates to a method of preparation hydrophobized hyaluronic acid and its use as carrying biologically active hydrophobic substances, wherein a biologically active substance is encapsulated into the nanomicelles of hydrophobized hyaluronan. The hydrophobization of hyaluronan is carried out through an esterification reaction of hyaluronan with long-chain carboxylic acids, the latter being activated by a halogenide derivative of 2,4,6-trichlorobenzoic acid or by another organic chloride of $R_3$—CO—Cl. In a suitable aqueous environment, water-soluble hydrophobized derivatives can form nanomicelles in which nonpolar substances can be bound by means of non-covalent physical interactions. The core of a nanomicelle is formed by hydrophobic acyl functional groups while the shell of a nanomicelle is formed by hyaluronic acid. The encapsulation of the substances into nanomicelles can be performed by means of the solvent exchange method or by means of sonication. Hyaluronic nanomicelles support the penetration of bound substances in topical applications and enable the bound substances to be transferred into the individual cells. The invention further relates to a method for preparing stabilized nanomicellar compositions. The nanomicelles obtained from hydrophobized hyaluronan derivatives are usable in cosmetic and pharmaceutical applications.

BACKGROUND OF THE INVENTION

Hyaluronic acid is an important polysaccharide consisting of two repeating units of β-(1,3)-D-glucuronic acid and β-(1,4)-N-acetyl-D-glucosamine. It is characterized by a high molecular weight ranging from $5.10^4$ to $5.10^6$ g·mol$^{-1}$ which depends on the isolation method and on the initial material used. Hyaluronic acid, and particularly its sodium salt known as hyaluronan, is and essential constituent of connective tissues and of synovial joint fluid. Moreover it plays a significant role in numerous biological processes, such as hydration, organization of proteoglycans, cellular differentiation, proliferation and angiogenesis. This polysaccharide, which is strongly hydrophilic, is water soluble in the form of salts within the entire pH scale.

Carrier Systems on the Basis of Hyaluronic Acid

Due to the hydrophilic nature of its native form, hyaluronic acid cannot serve as an effective carrier for hydrophobic substances. For this reason, hydrophobic functional groups have to be linked to a polymeric chain of hyaluronic acid. In case that such hydrophobic functional groups have sufficient quantities and lengths, an auto-aggregation process involving the same can be initiated resulting in the formation of hydrophobic domains within the structure of hyaluronan. Afterwards, small molecules of water insoluble substances can be linked to such domains by means of non-covalent bonds. The resulting structure is often referred to as polymeric nanomicelle in the literature. wherein the core of the micelle is hydrophobic, thus enabling the dissolution of small nonpolar molecules to take place, while the shell of the same is hydrophilic, thus enabling the polymeric micelle itself to be dissolved in an aqueous environment. A polymeric micelle, which does not exceed 200 nm in size (diameter), can be referred to as nanomicelle.

Carrier systems formed by polymeric micelles on the basis of modified hyaluronic acid are known from conjugates of hyaluronan with alkylamines (Liu et al., 2011) and folic acid. Nevertheless, the presence of highly toxic and teratogenic formamide is deemed to be essential for the preparation of the above hyaluronan derivative. A similar method of preparation of polymeric micelles was employed for obtaining redox-sensitive micelles (Li et al., 2011). It is obvious that such micellar systems are not usable in biological applications due to the presence of highly toxic reagents.

The conjugation of hyaluronic acid with other polymers (such as those of lactic or glycolic acids) through the bond mediated by the carboxylic group of D-glucuronic acid and possibly through the incorporation of low-molecular substances is claimed in the U.S. Pat. No. 7,767,806 wherein the authors mention the biocompatibility of the polymer which, however, has been neither described nor proved by tests. In another case, the low-molecular hyaluronan (9-45 kDa) was covalently modified (in the position of the carboxylic group of glucuronic acid) by hydrophobic amines having various chain lengths and by positively charged spermine used as a cationic segment (Shen. Li, Tu & Zhu, 2009). The purpose of the latter was to prepare a carrier for genes. However, the use of spermine for the above purpose is restricted due to its acute and subacute toxicity (Til, Falke, Prinsen & Willems, 1997). The critical micellar concentration of the formed polymeric micelles having 125-555 in diameter was determined to be higher than 0.04 mg·mL$^{-1}$. In addition to the fact that the value of the critical micellar concentration is too high and hence does not enable any extreme dilution of micellar system to be achieved (e.g. in the bloodstream), the micelles having the above mentioned size are not considered to be suitable candidates for the passive distribution of medicines within the human body because the size of a polymeric micelle is determinative for the ability of the same to reach a tumor location or infarct lesion through a disrupted venous wall. In such cases, polymeric micelles having 20-100 nm in diameter are preferred (Wang. Mongayt & Torchilin, 2005).

The modification of the carboxylic group of glucuronic acid was utilized for the preparation of polymeric hyaluronan micelles on the basis of the electrostatic interaction between negatively charged hyaluronic acid and positively charged styryl pyridinium (Tao, Xu, Chen, Bai & Liu, 2012). However, the use of such polymeric micelles in vivo is restricted due to the fact that the interactions of styryl pyridinium with nerve terminals and muscarine receptors has not been sufficiently clarified so far, although such interactions play an important role in connection with the regulation of releasing neurotransmitters from neurons (Mazzone, Mori, Burman, Palovich, Belmonte & Canning, 2006).

In the patent documents U.S. 7,993,678 and WO 2007/033677, the method of preparation alkyl/aryl-succinic derivatives of hyaluronan is claimed, such derivatives being also usable for the encapsulation of active nonpolar substances. In the latter case, the modification involves the primary hydroxyl groups of hyaluronan while the carboxylic group remains unchanged. A disadvantage of the above modification reaction is the alkaline pH range (pH 8.5-9.0) in which the reaction of cyclic anhydrides with hyaluronan takes place. In fact, such alkaline pH values can initiate the hydrolysis of anhydrides and, hence, cause the efficacy of the modification process to decrease. This would be particularly considerable in an industrial scale. In the alkyl/aryl-succinic derivatives of hyaluronan, which had been prepared in the above manner and had the substitution degree of 44%, the ability to form micelles (to aggregate) in an aqueous environment was proves when the respective concentration were higher than 0.003-0.004 mg·mL$^{-1}$. The observed size of the polymeric micelles ranged between 50 and 200 nm. The disadvantage of such derivatives, however, consists in the increase of the total negative charge of hyaluronan caused by the presence of an additional COO$^-$ group in the modifying alkyl/aryl-succinic functional group. The negative charge of the molecule may have a significant unfavourable influence on the interaction between cells and the respective carrier system (Wang, Mongayt & Torchilin, 2005). One of the limiting factors for the injection application of the derivatives prepared in the above manner consists in their low solubility (Eenschooten, Guillaumie, Kontogeorgis, Stenby & Schwach-Abdellaoui, 2010). Another disadvantage of such derivatives consists in the instability of the ester bonds during thermal sterilization processes, such as autoclaving ones. In the patent documents U.S. Pat. No. 7,993,678 and WO 2007/033677, merely the method of direct dissolution of nonpolar substances in the solutions of alkyl/aryl-succinic derivatives of hyaluronan, including the formation of a stable emulsion, is described. The main disadvantage of the direct method of encapsulation of nonpolar substances consists in the low resulting bonding capacities of polymeric micelles (Kedar, Phutane, Shidhaye & Kadam, 2010). Although the above patents claim the utilization of the structure of modified hyaluronan for carrier systems, they do not provide any further possible way of linking a hydrophobic substance to the given structure of hyaluronan in addition to the emulsion system. For this reason, the provision both a polymeric carrier system having a sufficient bonding capacity is completely missing which would be one of the basic characteristics required for a realistic assessment of applicability. Moreover, no details relating to cytotoxicity and cellular interactions are mentioned and hence it is not possible to a conclusion about whether the claimed structure is actually applicable for an active transfer of hydrophobic substances into cells, which conclusion is essential in pharmaceutical applications.

In a further publication (Šmejkalová, Hermannová, Šuláková, Průšová, Kučerík & Velebný, 2012), hydrophobic domains of hyaluronan are described which originate from the aggregation of C6-acyl chains linked to hyaluronan by covalent bonds. The derivatives described in the latter publication, however, are not entirely free from residual solvents. Besides that, neither the formation nor the characterization of polymeric micelles is discussed in the above publication. Moreover, the symmetrical anhydrides mentioned in the above publication are not usable for the formation of bonds between long alkyl chains. Carboxylic acids having long aliphatic chains are very expensive and, on top of that, at least one mole of acid gets lost during the preparation of one mole of the final reagent. The publication does not discuss the cytotoxicity of the prepared derivatives, either.

The preparation of butyric esters of polysaccharides including a corresponding pharmaceutical composition is claimed in the patent EP 0941253. The claimed methodology of preparation, however, enables only very low degrees of substitution to be achieved (3% max.). The quantity of the hydrophobic substance. which is linked to the prepared derivatives by means of a non-covalent bond, is unfavourably influenced by such a low degree of substitution. The butyric esters of hyaluronan were further prepared in accordance with the patent WO 2005/092929 wherein, however, non-aqueous conditions. Consequently, the transformation of hyaluronan into a quaternary ammonium salt may be accompanied by the degradation of hyaluronan. The achieved degree of substitution is lower than 0.1% and therefore such ester derivatives are not suitable for the preparation of carrier systems. Similar results were obtained when the simultaneous esterification of hyaluronan with the anhydride of butyric acid and the chloride of retinoic acid was carried out (WO 2004/056877).

A composition of polymeric micelles on the basis of modified hyaluronan (HA)-[O(C=O)NH-M]$_p$, wherein M represents a modifying unit comprising the alkyl functional group $C_{2-16}$ and p represents a multiple of 3-4, and pharmaceutically active molecules is claimed by the patents U.S. 2010/0316682 and EP1538166A1. The main drawback of such derivatives consists in that dibutyltin laurate, which is known as a substance having an immunotoxic and teratogenic potential, is used for performing the modification of hyaluronan. The latter substance is mostly used in the modification processes related to the production of adhesives and is listed by the European Environment Agency due to its acute toxicity (Boyer, 1989). Another drawback of the claimed derivatives consists in their conjugation with polymers, e.g. with polyethylene glycol, which are extraneous in relation to the human body and can cause inflammatory reactions or give rise cytotoxic degradation products when used for intravenous or topical applications. Moreover, repeated application of polymeric micelles, where polyethylene glycol formed the hydrophilic segment, led to accelerated elimination of those micelles from the bloodstream due to the formation of anti-PEG IgM antibodies (Gong, Chen, Zheng. Wang & Wang, 2012).

Paclitaxel was successfully incorporated into the micelles of modified hyaluronan by means of poly lactic-co-glycolic acid (PLGA) (Kim, Lee, Jang & Park, 2009). The incorporation was carried out with the use of a dialythic method wherein both the polymer and the respective bound substance were dissolved in DMSO and the resulting solution was dialyzed against $H_2O$. In the latter case, the bonding capacity of prepared polymeric micelles of 4.5% by weight was obtained. The main disadvantage of such carrier systems consists in the presence of PLGA polymers, which are extraneous with respect to the human body and may not represent a fully biodegradable system. Another disadvantage consists in the presence of residual DMSO in the final products.

Modification of Hyaluronan with Long-Chain Carboxylic Acids

The modification of polysaccharides with carboxylic acids mostly requires a commercially available anhydride of the given acid (WO 1996/035720. WO 2007/033677. (Šmejkalová, Hermannová, Šuláková, Průšová, Kučerík & Velebný, 2012), EP 0893451). The main disadvantages of such commercially available anhydrides consist in their susceptibility to hydrolysis and in the possible presence of impurities. Moreover, anhydrides of some acids (e.g. undecane-carboxylic acids) are not commercially available. Some of the available anhydrides are very expensive (e.g. those of oleic, linoleic or linolenic acids). Thus, the unavailability, high price and instability of such anhydrides make the large-scale preparation of modified polysaccharides difficult.

Acid anhydrides can be substituted with other acid derivatives which are usable for the esterification of hyaluronan.

The patent WO 2010/105582 claim the method of activation of carboxylic acids by means of ethylchloroformiate in non-aqueous conditions, wherein O-acyl-O'-alkyl carbonates are formed which are subsequently usable for the esterification of hyaluronan. The disadvantage of such activation consists in the formation of toxic and potentially explosive gases. A similar method of activation with ethylchloroformiate is disclosed in the patents U.S. Pat. No. 3,720,662 and CZ 20060605.

Another known method is based on the esterification of polysaccharides with carboxylic acids under presence of imidazole (U.S. 2012/0172587). However, the claimed method of preparation requires high reaction temperatures (90-200° C.) which are not applicable to hyaluronan due its degradation under elevated temperatures.

The European patent EP 0893451 claims the esterification of polysaccharides with anhydrides carboxylic acids by means of the method of supercritical extraction. The disadvantages of the latter esterification procedure consist in the necessary high pressure and in the high equipment cost.

For the above reasons, it is very important to find an alternative method of activation of long-chain carboxylic acids, which method would be an in-situ applicable one. One of the possible technical solutions is based on the activation of carboxylic acids with a derivative of 2,4,6-trichlorobenzoic acid accompanied by the formation of an anhydride. For the first time, an anhydride of 2,4,6-trichlorobenzoic acid was used in combination with the DMAP catalyst for a rapid esterification of macrocyclic substances under moderate reaction conditions (Inanaga, Hirata, Saeki, Katsuki & Yamaguchi, 1979). This method of esterification. however, has not yet been applied to the modification of polysaccharides, particularly of hyaluronic acid, because of the possible exothermic reaction accompanied with the degradation of the respective polysaccharide.

SUMMARY OF THE INVENTION

The subject matter of the present invention is the synthesis of a hydrophobized derivative of hyaluronic acid and the application of said derivative in the form of a polymeric carrier for biologically active hydrophobic substances in aqueous environment, wherein the native character and the biological activity of the bound substances should remain unchanged.

The hydrophobization of hyaluronan with long-chain aliphatic esters (C6-C18) is based on the direct activation of long-chain carboxylic acids accompanied with the formation of an anhydride of 2,4,6-trichlorobenzoic acid (Scheme 1). In the next step, the resulting anhydride reacts with hyaluronic acid to form an acylated derivative of hyaluronic acid. The principal advantage of said activation consists in the possibility of the direct application of aliphatic carboxylic acids. Unlike the similar hydrophobizing reactions of hyaluronan, which constitute the prior art, the presented modification doesn't require any commercially available anhydride to be used. Another advantage of the presented activation consists in the fact that the respective reaction can take place under moderate conditions (from the room temperature up to 50° C.) and has a short duration. Furthermore, the presented activation requires, unlike the method disclosed in the patent application WO 2010/105582, neither an excessive quantity of aliphatic acids nor special anhydrous conditions. The activating reagent is stable and, unlike ethylchloroformiate, does not cause the production of toxic or explosive gases when used in the reaction. Another advantage of the presented activating reagent consists in that the reagent does not form any reaction by-products and does not induce cross-linking reactions.

The activation of carboxylic acids with a derivative of 2,4,6-trichlorobenzoic acid with the subsequent application of the resulting activated product to the esterification of hyaluronic acid is depicted in the scheme 1 below:

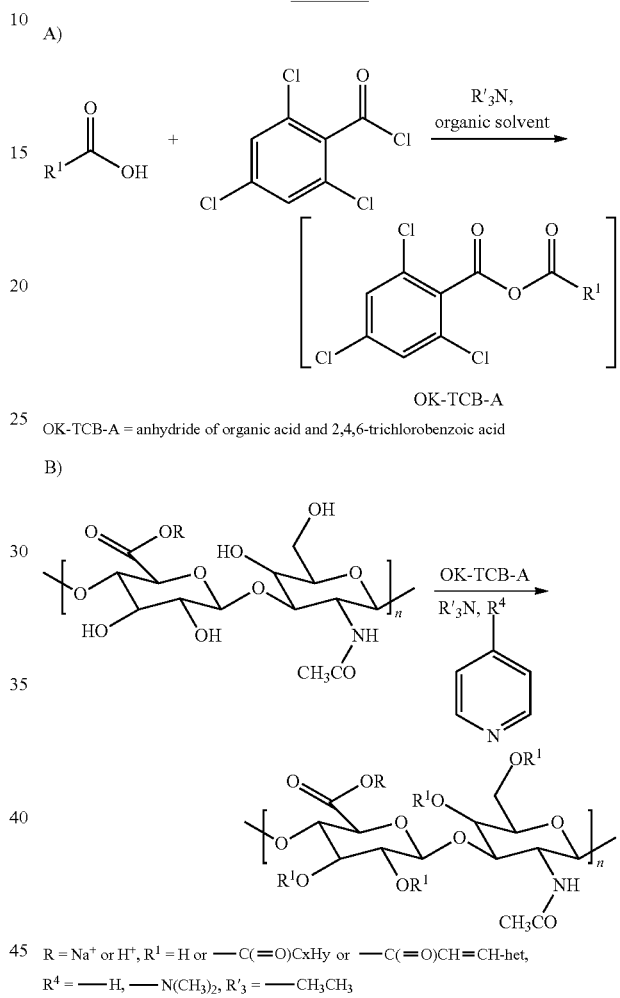

Scheme 1.

A)

OK-TCB-A

OK-TCB-A = anhydride of organic acid and 2,4,6-trichlorobenzoic acid

B)

R = $Na^+$ or $H^+$, $R^1$ = H or —C(=O)CxHy or —C(=O)CH=CH-het, $R^4$ = —H, —$N(CH_3)_2$, $R'_3$ = —$CH_3CH_3$ Furthermore, the invention relates to the use of hydrophobized hyaluronic acid for preparation of nanomicellar systems and to the application of the substances bound in the nanomicelles of hyaluronic acid for the treatment of skin, hair and mucous membranes, other topical applications being also possible. The encapsulated biologically active substances are bound in the nanomicelles of hyaluronan by non-covalent physical interactions with hydrophobic functional groups of the polymeric carrier. When encapsulated in the above manner, such substances effectively penetrate into the superficial skin layer (epidermis), into the entire structure of hairs and into the epithelium of mucous membranes. One of the advantages consists in that the penetration depth of the active substances hound in the nanomicelles is greater that that of the same substances when the latter are directly dissolved in nonpolar solvents.

In comparison with similar polymeric systems (such as those disclosed in the patents U.S. 7,993,678 and WO 2007/033677), the nanomicellar conjugates of hyaluronan have unexpectedly exhibited a 3-fold to 10-fold lower critical micellar concentration and, simultaneously, a relatively high stability in salty and aqueous environments. Such a very low value of the critical micellar concentration is particularly advantageous in connection with possible intravenous applications of hyaluronan micelles. Contrary to the similar systems based on the most of other known polymers, as described with reference to the prior art, the high stability of hyaluronan micelles may be advantageous in connection with the lyophilisation of various materials because the desired encapsulation can be preserved without adding any lyoprotectant to the solution before freezing.

Another advantage of the claimed hydrophobized derivatives of hyaluronan is related to the absence of synthetic polymers (PLGA, PEG, etc.) and copolymers which are otherwise often necessary for the formation of nanomicelles and which can trigger the creation of antibodies when administered repeatedly (Gong, Chen, Wang & Wang).

Contrary to similar polymeric micellar systems, the formation of nanomicelles is not based on a modified hyaluronan having an increased total negative charge, and thus the interaction between the carrier system with cells is not unfavourably influenced by such charge.

Some of the nanomicellar structures, particularly those containing longer acyl chains linked to hyaluronan, may form a gel phase in an aqueous environment. Such a gel phase may be advantageously used in certain applications requiring and increased viscosity of the respective carrier system.

The dimensions of the prepared nanomicellar systems mostly range between 20 and 100 nm, which is an optimum size for pharmaceutical applications in which the advantage of the enhanced permeability and retention effect (EPR effect) is taken. Such size may not be always achievable in polymeric micelles described with reference to the prior art.

Another advantage of the hyaluronan micelles is related to the transfer of bound substances from the hydrophobic domains of a nanomicelle into a cell.

The innovated encapsulating method is based on the preparation of a mixture of hyaluronan dissolved in water and a biologically active substance dissolved in an organic solvent, followed by the energetic disruption of the hydration envelope of hyaluronan and subsequent removal of the solvent from the solution. In contrast to common encapsulating procedures, the above method is not based on the solubility of polymers in an organic solvent and hence does not require the native character of hyaluronic acid to be suppressed and the polymeric chain to be largely modified, particularly in the location of the important carboxylic groups which enable hyaluronan to be recognized by cellular receptors. A preferred organic solvents is that having a lower boiling point than water. The bonding capacity of hyaluronan nanomicelles is markedly increased by the complete evaporation of the residual aqueous phase with the subsequent rehydration of nanomicelles. An unbound biologically active substance can be eliminated in a filtration process and the resulting nanomicelles can be directly lyophilized and stored in dry state until the time of the subsequent rehydration.

Specifically, the invention relates to a $C_6$-$C_{18}$-acylated derivative of hyaluronic acid according to the general formula (I):

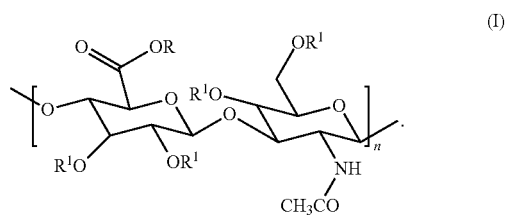

wherein R represents $H^+$ or $Na^+$ and $R^1$ represents H or —C(=O)$C_xH_y$, or —C(=O)CH=CH-het, where x is an integer ranging between 5 and 17 and y is an integer ranging between 11 and 35 and $C_xH_y$ is a linear or branched, saturated or unsaturated $C_5$-$C_{17}$ chain and het is a heterocyclic or heteroaromatic group having a selectable content of N, S or O atoms, at least one repeating unit being one or more $R^1$—C(=O)$C_xH_y$, or —C(=O)CH=CH-het groups, and wherein n ranges between 12 and 4000. In a preferred embodiment of the invention, the $C_6$-$C_{18}$-acylated derivative is an oleyl derivative which means that R represents $H^+$ or $Na^+$ and $R^1$ represents —C(=O)(CH$_2$)$_7$—CH=CH—(CH$_2$)$_7$CH$_3$ in the formula (I).

Furthermore, the invention relates to the method of preparation of the above derivative of hyaluronic acid, wherein hyaluronic acid reacts with $C_6$-$C_{18}$-carboxylic acid activated with a chloride of 2,4,6-trichlorobenzoic acid or activated with an organic chloride of $R_3$—CO—Cl under presence of a base and a catalyst in a mixture of water and a water-miscible aprotic solvent, where $R_3$ is an aliphatic or branched $C_1$-$C_{30}$-alkyl occasionally containing heteroaromatic or aromatic functional groups. An exemplary heteroaromatic functional group may be pyridine along with its derivatives (e.g. according to the formula (i)), an exemplary aromatic functional group may benzene along with its halogen derivatives (e.g. according to the formula (ii)).

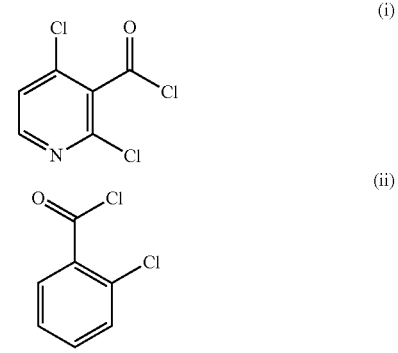

Hyaluronic acid may assume the free acidic form or the form of a pharmaceutically acceptable salt, such as a Na, K, Ca, Mg, Zn, or Li salt, and have a molecular weight ranging preferably between $5\times10^3$ g/mol and $1.6\times10^6$ g/mol, more preferably between $15\times10^3$ g/mol and $250\times10^3$ g/mol, and most preferably between $15\times10^3$ and $50\times10^3$ g/mol. The method of preparation according to the invention consists in that hyaluronic acid is dissolved in a mixture of water and a water-miscible aprotic solvent, the latter being a polar organic solvent, the water content being in the range between 10 and 99% by volume, preferably 50% by volume. The water-miscible aprotic solvent may be, for example, dimethyl sulfoxide (DMSO), tetrahydrofuran (THF), acetone, acetonitrile or isopropanol (WA). The reaction mixture contains an R′₃N base, wherein R′ is a linear or branched $C_nH_m$ hydrocarbon chain, wherein n is an integer ranging between 1 and 4 and m is an integer ranging between 3 and 9, e.g. triethylamine, in the amount of 0.01 to 20 equivalents, preferably 6 equivalents, relative to a dimer of hyaluronic acid, and the catalyst is selected from the group comprising substituted pyridinines, such as dimethylaminopyridine, in the amount of 0.01 to 1 equivalent, preferably 0.05 equivalent, relative to a dimer of hyaluronic acid. In the method of preparation according to the invention, first the activation of $C_6$-$C_{18}$-carboxylic acid is performed in a polar organic solvent under the presence of a base and of 2,4,6-trichlorobenzoic acid or its derivatives or under the presence of a base and an organic chloride and subsequently the mixture containing activated $C_6$-$C_{18}$-carboxylic acid is added to hyaluronic acid, which was dissolved in a mixture of water, an organic solvent, a base and a catalyst, the product of the resulting reaction being the derivative according to the general formula (I). Said $C_6$-$C_{18}$-carboxylic acid is selected from the group containing caproic, enanthic. caprylic, capric, palmitic. stearic. oleic, linoleic and linolenic acids. The amount of activated $C_6$-$C_{18}$-carboxylic acid ranges between 0.01 and 5 equivalents, preferably between 0.5 and 2 equivalents. relative to a dimer of hyaluronic acid. The activation of $C_6$-$C_{18}$-carboxylic acid takes places for 5 to 120 minutes, preferably for 30 minutes, under the temperature between 20 and 60° C., preferably under the temperature of 25° C. The reaction of hyaluronic acid with activated $C_6$-$C_{18}$-carboxylic acid takes places for 1 to 24 hours, preferably for 2 to 3 hours, under the temperature between 20 and 60° C., preferably under the temperature of 25° C. The $C_6$-$C_{18}$-acylated derivative of hyaluronic acid may be subsequently separated from the reaction mixture, washed, dried and lyophilized. The derivative may be separated from the reaction mixture by precipitation using NaCl and alcohol. Subsequently, the derivative may be washed with alcohol, particularly with isopropanol or ethanol.

In a further aspect, the invention relates to a nanomicellar composition on the basis of a $C_6$-$C_{18}$-acylated derivative of hyaluronic acid according to the general formula (I), which composition contains nanomicelles which comprise a hydrophobic core formed by $C_6$-$C_{18}$-acyl groups linked to hyaluronic acid and a hydrophilic shell formed by hydrophilic functional groups of hyaluronic acid. one or more biologically active substances being physically bound in each nanomicelle. The composition further contains water and may also contain salts (e.g. 0.9% NaCl). In a preferred embodiment, the nanomicellar composition contains 0.3 to 50% by weight of a biologically active substance relative to the mass content of the $C_6$-$C_{18}$-acylated derivative of hyaluronic acid, the biologically active substance being selected from a group comprising pharmaceutically and cosmetically active substances. particularly vitamins, medicines, cytostatics, phytoextracts, phytocomplexes or phytoactive substances, mineral or vegetable oils, or a mixture thereof. The examples of applicable biologically active substances include, e.g., tocoferol, paclitaxel, phosphatidylcholine or coenzyme Q10. In a preferred embodiment, the composition contains a $C_6$-$C_{18}$-acylated derivative of hyaluronic acid in a concentration which is higher than its critical aggregation concentration. The concentration of the $C_6$-$C_{18}$-acylated derivative of hyaluronic acid ranges between 0.0001 mg·mL⁻¹ and 30 mg·mL⁻¹, preferably between 1 and 20 mg·mL⁻¹, when the composition is in an aqueous solution. In another preferred embodiment, the biologically active substance is a mineral or vegetable oil contained in the amount of 0.05 to 40% by weight, preferably 1 to 20% by weight, relative to the mass content of the $C_6$-$C_{18}$-acylated derivative of hyaluronic acid. In yet another preferred embodiment, the composition contains a biologically active substance which is liquid and insoluble in water, said substance containing an additional biologically active substance dissolved therein. Such biologically active substance, which is liquid and insoluble in water, may be, e.g., a mineral or vegetable oil, and the additional biologically active substance may belong, e.g., among pharmaceutically or cosmetically active substances, particularly vitamins, medicines. cytostatics, phytoextracts, phytocomplexes or phytoactive substances, or mixtures thereof. The nanomicellar composition according to the invention may assume the form of a solution, nanoemulsion, microemulsion, coacervate or gel.

The invention further relates to the method of preparation of the nanomicellar composition as defined above, wherein the $C_6$-$C_{18}$-acylated derivative of hyaluronic acid according to the general formula (I) is dissolved in water, the biologically active substance is dissolved in an organic solvent, the resulting solutions are mixed together and afterwards the organic solvent is removed. The organic solvent may be a volatile chlorinated solvent, such as trichloromethane, or an alcohol, such as ethanol or isopropanol. and its removal may take place by vacuum evaporation. Subsequently the aqueous phase is dried and rehydrated and the resulting nanomicellar structures are filtered and finally lyophilized. Alternatively, the organic solvent may be removed by dialysis. Again, the resulting nanomicellar structures are subsequently filtered and finally lyophilized. In a preferred embodiment, the $C_6$-$C_{18}$-acylated derivative of hyaluronic acid according to the general formula (I) is dissolved in water and subsequently mixed together with a biologically active substance, which is liquid and insoluble in water, whereupon the resulting mixture is homogenized by sonication to form a microemulsion or nanoemulsion. In another preferred embodiment, the $C_6$-$C_{18}$-acylated derivative of hyaluronic acid according to the general formula (I) is dissolved in water and subsequently mixed together with a biologically active substance, which is liquid and insoluble in water and in which an additional biologically active substance is dissolved, whereupon the resulting mixture is homogenized by sonication to form a microemulsion or nanoemulsion.

In yet another aspect, the invention relates to the use of the nanomicellar composition in pharmaceutical or cosmetic applications, preferably in topical application.

Furthermore, a stabilized nanomicellar composition may be prepared. The method of preparation of such a stabilized nanomicellar composition consists in that $C_6$-$C_{18}$-acylated hyaluronan according to the general formula (II) is prepared:

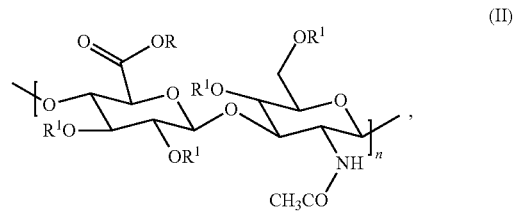

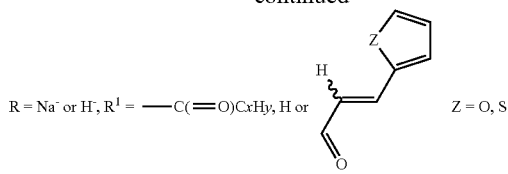

wherein R represents H⁺ or Na⁺, one or more R¹ members are represented by a linear $C_6$-$C_{18}$-chain in at least one repeating unit, which linear chain can contain unsaturated bonds, and by 3-(2-thienyl)acrylic acid or by 3-(2-furyl) acrylic acid or by derivatives of said acids in another at least one repeating unit, whereupon a nanomicellar composition is prepared from the $C_6$-$C_{18}$-acylated hyaluronan according to the general formula (II), which composition is then stabilized in a cross-linking reaction.

In particular, the stabilization is carried out in the following manner: first, the derivative according to the general formula (III) is prepared:

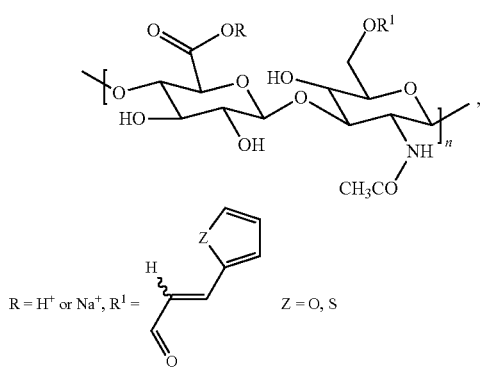

in that hyaluronic acid is dissolved in water and afterwards a base (such as TEA) and a catalyst (DMAP); in a separate procedure, activated 3-(2-thienyl)acrylic acid or 3-(2-furyl) acrylic acid or a derivative of either acid is prepared, the activation taking place in a mixture of an organic solvent (e.g. THF) and a base (e.g. TEA) with the addition of an chloride of 2,4,6-trichlorobenzoic acid, and finally both mixtures are mixed together to form acrylated hyaluronan according to the formula (III). Subsequently, activated $C_6$-$C_{18}$-carboxylic acid is prepared for the acylation of said acrylated hyaluronan according to the formula (III) in a manner, which is similar to that described above with reference to the method of preparation $C_6$-$C_{18}$-acylated hyaluronan according to the general formula (I), to form acylated hyaluronan according to the formula (I). Finally, nanomicelles may be analogously prepared from the acylated hyaluronan which has been prepared in the above manner. Such nanomicelles may be subsequently cross-linked in radical reactions, e.g. using ammonium peroxydisulfate. Such cross-linked hyaluronan is not soluble in water.

LITERATURE CITED

Boyer. I. J. (1989). Toxicity of dibutyltin, tributyltin and other organotin compounds to humans and to experimental animals. Toxicology, 55(3), 253-298.

Eenschooten, C., Guillaumie, F., Kontogeorgis, G. M., Stenby, E. H., & Schwach-Abdellaoui, K. (2010). Preparation and structural characterisation of novel and versatile amphiphilic octenyl succinic anhydride-modified hyaluronic acid derivatives. Carbohydrate Polymers, 79(3), 597-605.

Gong, J., Chen, M., Zheng, Y., Wang, S., & Wang, Y. (2012). Polymeric micelles drug delivery system in oncology. Journal of Controlled Release, 159(3), 312-323.

Inanaga, J., Hirata, K., Saeki, H., Katsuki, T., & Yamaguchi, M. (1979). A Rapid Esterification by Means of Mixed Anhydride and Its Application to Large-ring Lactonization. Bulletin of the Chemical Society of Japan, 52(7), 1989-1993.

Kedar, U., Phutane, P., Shidhaye, S., & Kadam, V. (2010). Advances in polymeric micelles for drug delivery and tumor targeting. Nanomedicine: Nanotechnology, Biology and Medicine. 6(6), 714-729.

Kim, T. G., Lee, H., Jang, Y., & Park, T. G. (2009). Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel. Biomacromolecules, 10(6), 1532-1539.

Li, J., Huo, M., Wang, J., Zhou, J., Mohammad, J. M., Zhang, Y., Zhu, Q., Waddad, A. Y., & Zhang, Q. (2012). Redox-sensitive micelles self-assembled from amphiphilic hyaluronic acid-deoxycholic acid conjugates for targeted intracellular delivery of paclitaxel. Biomaterials, 33(7), 2310-2320.

Liu, Y., Sun, J., Cao. W., Yang, J., Lian, H., Li, X., Sun, Y., Wang, Y., Wang, S., & He, Z. (2011) Dual targeting folate-conjugated hyaluronic acid polymeric micelles for paclitaxel delivery. International Journal of Pharmaceutics, 421(1), 160-169.

Mazzone, S. B., Mori, N., Burman. M., Palovich, M., Belmonte, K. E., & Canning, B. J. (2006). Fluorescent styryl dyes FM1-43 and FM2-10 are muscarinic receptor antagonists: intravital visualization of receptor occupancy. The Journal of Physiology, 575(1), 23-35.

Shen, Y., Li, Q., Tu, J., & Zhu, J. (2009). Synthesis and characterization of low molecular weight hyaluronic acid-based cationic micelles for efficient siRNA delivery. Carbohydrate Polymers, 77(1), 95-104.

Šmjkalová, D., Herinannova, M., Suláková, R., Průšová, A., Kučerik, J., & Velebný, V. (2012). Structural and conformational differences of acylated hyaluronan modified in protic and aprotic solvent system. Carbohydrate Polymers, 87(2), 1460-1466.

Tao. Y., Xu, J., Chen, M., Bai, H., & Liu, X. Core cross-linked hyaluronan-styrylpyridinium micelles as a novel carrier for paclitaxel. (2012). Carbohydrate Polymers, 88(1), 118-124.

Til, H. P., Falke, H. E., Prinsen, M. K., & Willems, M. I. (1997). Acute and subacute toxicity of tyramine, spermidine, spermine, putrescine and cadaverine in rats. Food and Chemical Toxicology, 35(3-4), 337-348.

Wang, J., Mongayt, D., & Torchilin, V. P. (2005). Polymeric micelles for delivery of poorly soluble drugs: Preparation and anticancer activity in vitro of paclitaxel incorporated into mixed micelles based on poly(ethylene glycol)-lipid conjugate and positively charged lipids. Journal of Drug Targeting, 13(1), 73-80.

EXAMPLES OF PREFERRED EMBODIMENTS OF THE INVENTION

Figure 1:
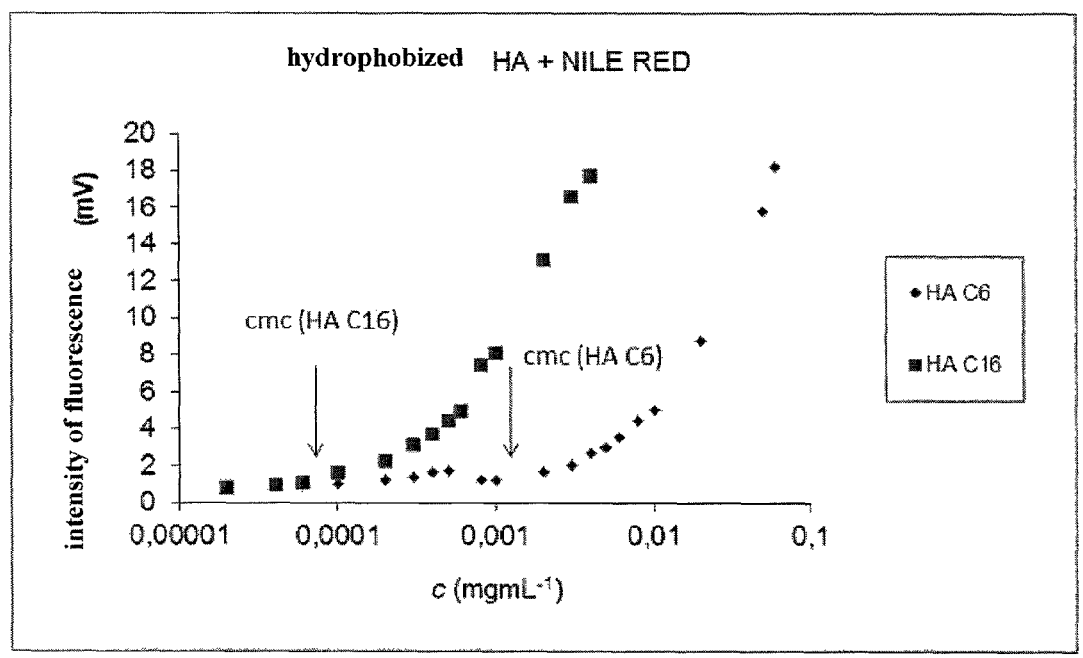
FIG. 1. Determination of the critical micellar (aggregation) concentration (CMC) using the fluorescence method on the acylated hyaluronan derivative (C6) and (C16) with encapsulated Nile red in water.

DS=degree of substitution=100%*molar amount of the bound substituent/molar amount of all the polysaccharide dimers Unless otherwise specified, the expression "equivalent" (eq) as used herein refers to a dimer of hyaluronic acid. Unless otherwise specified, percentages are figured on a weight/weight basis.

The molecular weight of the primary hyaluronic acid (source: Contipro Biotech spol. s r.o., Dolní Dobrouč, Czech Republic) was determined by means of the SEC-MALLS method.

Example 1

Preparation of Capronyl (C6) Derivative of Hyaluronic Acid by Means of the Mixed Anhydride of 2,4,6-Trichlorohenzoic Acid and Caproic Acid 1 g of sodium hyaluronate (2.5 mmol. 15 kDa) was dissolved in 10 mL of demineralized water. Afterwards, 5 mL of DMSO were gradually added. Then, TEA (1.05 mL, 3 eq.) and DMAP (8.0 mg, 0.05 eq.) were added to the solution. Simultaneously, hexanoic acid (0.63 mL, 2 eq.) was dissolved in 5 mL of DMSO and TEA (1.05 mL, 3 eq.) and then 2,4,6-trichlorobenzoyl chloride (1.6 mL. 4 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.25 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMSO and DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 60% (determined from NMR)
$^1$H NMR (D$_2$O) signals of acyl: δ 2.4 ppm (m, 2H, α CH$_2$), δ 1.6 ppm (m, 2H, β CH$_2$), δ 1.3 ppm (m, 4H, γ, δ CH2), δ 0.8 (m, 3H, CH$_3$).

Example 2

Preparation of Capronyl (C6) Derivative of Hyaluronic Acid by Means of the Mixed Anhydride of 2,4,6-Trichlorobenzoic Acid and Caproic Acid 1 g of sodium hyaluronate (2.5 mmol, 38 kDa) was dissolved in 10 mL of demineralized water. Afterwards, 5 mL of isopropanol were gradually added. Then, TEA (1.05 mL, 3 eq.) and pyridine (0.4 mL, 2.0 eq.) were added to the solution. Simultaneously, hexanoic acid (0.32 mL. 1 eq.) was dissolved in 5 mL of isopropanol and then TEA (1.05 mL, 3 eq.) and 2,4,6-trichlorobenzoyl chloride (0.391 mL, 1 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.50 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove pyridine from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 15% (determined from NMR)
$^1$H NMR (D$_2$O) signals of acyl: δ 2.4 ppm (m, 2H, α CH$_2$), δ 1.6 ppm (m, 2H, β CH$_2$), δ 1.3 ppm (m, 4H, γ, δ CH2), δ 0.8 (m, 3H, CH$_3$).

Example 3

Preparation of Enanthyl (C7) Derivative of Hyaluronic Acid by Means of the Mixed Anhydride of 2,4,6-Trichlorobenzoic Acid and Enanthic Acid 1 g of sodium hyaluronate (2.5 mmol, 15 kDa) was dissolved in 10 mL of demineralized water. Afterwards, 5 mL of acetonitrile were gradually added. Then, TEA (0.70 mL, 2 eq.) and DMAP (15.0 mg, 0.05 eq.) were added to the solution. Simultaneously, enanthic acid (0.35 mL, 1 eq.) was dissolved in 5 mL of acetonitrile and then TEA (0.70 mL, 2 eq.) and 2,4,6-trichlorobenzoyl chloride (0.39 mL, 1 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.75 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove acetonitrile and DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 12% (determined from NMR)

$^1$H NMR (D$_2$O) signals of acyl: δ 2.4 ppm (m, 2H, α CH$_2$), δ 1.6 ppm (m, 2H, β CH$_2$), δ 1.3 ppm (m, 6H, γ, δ,ε (CH$_2$)$_3$), δ 0.8 (m, 3H, CH$_3$).

Example 4

Preparation of Caprylyl (C8) Derivative of Hyaluronic Acid by Means of the Mixed Anhydride of 2,4,6-Trichlorobenzoic Acid and Caprylic Acid 1 g of sodium hyaluronate (2.5 mmol, 15 kDa) was dissolved in 10 mL of demineralized water. Afterwards, 5 mL of acetonitrile were gradually added. Then, TEA (1.05 mL, 3 eq.) and DMAP (8.0 mg. 0.05 eq.) were added to the solution. Simultaneously, octanoic acid (0.63 g, 4 eq.) was dissolved in 5 mL of acetonitrile and then TEA (1.05 mL, 3 eq.) and 2,4,6-trichlorobenzoyl chloride (0.8 mL, 4 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.50 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove acetonitrile and DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 40% (determined from NMR)

$^1$H NMR (D$_2$O) signals of acyl: δ 2.4 ppm (m, 2H, α CH$_2$), δ 1.6 ppm (m, 2H, β CH$_2$), δ 1.3 ppm (m, 8H, (CH$_2$)$_4$), δ 0.8 (m, 3H, CH$_3$).

Example 5

Preparation of Caprinyl (C10) Derivative of Hyaluronic Acid by Means of the Mixed Anhydride of 2,4,6-Trichlorobenzoic Acid and Capric Acid 1 g of sodium hyaluronate (2.5 mmol, 15 kDa) was dissolved in 10 mL of demineralized water. Afterwards, 5 mL of THF were gradually added. Then. TEA (1.05 mL, 3 eq.) and DMAP (8.0 mg, 0.025 eq.) were added to the solution. Simultaneously, decanoic acid (0.8 g, 2 eq.) was dissolved in 5 mL of THF and then TEA (1.05 mL, 3 eq.) and 2,4,6-trichlorobenzoyl chloride (0.8 mL, 2 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.25 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 15% (determined from NMR)

$^1$H NMR (D$_2$O) signals of acyl: δ 2.4 ppm (m, 2H, α CH$_2$), δ 1.6 ppm (m, 2H, β CH$_2$), δ 1.3 ppm (m, 12H, γ, δ, ε, ξ, η, θ CH$_2$), δ 0.8 (m, 3H, CH$_3$).

Example 6

Preparation of the Caprinyl (C10) Derivative of Hyaluronic Acid by Means of the Mixed Anhydride of 2,4,6-Trichlorobenzoic Acid and Capric Acid 1 g of sodium hyaluronate (2.5 mmol, 15 kDa) was dissolved in 10 mL of demineralized water. Afterwards, 5 mL of THF were gradually added. Then, TEA (1.05 mL, 3 eq.) and DMAP (8.0 mg, 0.025 eq.) were added to the solution. Simultaneously, decanoic acid (0.8 g, 4 eq.) was dissolved in 5 mL of THF and then TEA (1.05 mL, 3 eq.) and 2,4,6-trichlorobenzoyl chloride (0.8 mL, 4 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.25 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove THF and DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 40% (determined from NMR)

$^1$H NMR (D$_2$O) signals of acyl: δ 2.4 ppm (m, 2H, α CH$_2$), δ 1.6 ppm (m, 2H. β CH$_2$), δ 1.3 ppm (m, 12H, γ, δ, ε, ξ, η, θ CH$_2$), δ 0.8 (m, 3H, CH$_3$).

Example 7

Preparation of Palmitoyl (C16) Derivative of Hyaluronic Acid by Means of the Mixed Anhydride of 2,4,6-Trichlorobenzoic Acid and Palmitic Acid 0.5 g of sodium hyaluronate (1.25 mmol, 38 kDa) were dissolved in 20 mL of demineralized water. Afterwards, 10 mL of THF were gradually added. Then, TEA (0.52 mL, 3 eq.) and DMAP (8.0 mg, 0.05 eq.) were added to the solution. Simultaneously, palmitic acid (0.16 g, 0.5 eq.) was dissolved in 10 mL of THF and then TEA (0.52 mL, 3 eq.) and 2,4,6-trichlorobenzoyl chloride (0.098 mL, 0.5 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.25 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

$^1$H NMR ($D_2O$) signals of acyl: δ 2.4 ppm (m, 2H, α $CH_2$), δ 1.6 ppm (m, 2H, β $CH_2$), δ 1.3 ppm (m, 24H, $(CH_2)_{12}$), δ 0.8 (m, 3H, $CH_3$). DS 14% (determined from NMR)

Example 8

Preparation of Stearyl (C18) Derivative of Hyaluronic Acid by Means of the Mixed Anhydride of 2,4,6-Trichlorobenzoic Acid and Stearic Acid 0.5 g of sodium hyaluronate (1.25 mmol, 15 kDa) were dissolved in 10 mL of demineralized water. Afterwards, 5 mL of THF were gradually added. Then, TEA (0.52 mL, 3 eq.) and DMAP (8.0 mg, 0.05 eq.) were added to the solution. Simultaneously, stearic acid (0.711 g, 2 eq.) was dissolved in 5 mL of THF and then TEA (0.52 mL, 3 eq.) and 2,4,6-trichlorobenzoyl chloride (0.391 mL 2 eq.) were added to the solution. Following the activation of the acid, the precipitate was filtered into the prepared solution of HA. The reaction was taking place under the room temperature for 3 hours and subsequently the reaction mixture was being warmed up at 50° C. for 1 hour. Afterwards, the reaction mixture was diluted with 5 mL of demineralized water containing the addition of 0.25 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 7% (determined from NMR) $^1$H NMR ($D_2O$) signals of acyl: δ 2.4 ppm (m, 2H, α $CH_2$), δ 1.6 ppm (m, 2H, β $CH_2$), δ 1.3 ppm (m, 28H, $(CH_2)_{14}$), δ 0.8 (m, 3H, $CH_3$).

Example 9

Preparation of Oleyl (C18:1) Derivative of Hyaluronic Acid by Means of the Mixed Anhydride of 2,4,6-Trichlorobenzoic Acid and Oleic Acid 0.5 g of sodium hyaluronate (1.25 mmol, 15 kDa) were dissolved in 10 mL of demineralized water. Afterwards, 5 mL of THF were gradually added. Then, TEA (0.52 mL, 3 eq.) and DMAP (15.0 mg, 0.1 eq.) were added to the solution. Simultaneously, oleic acid (0.18 g, 0.5 eq.) was dissolved in 5 mL of THF and then TEA (0.52 mL, 3 eq.) and 2,4,6-trichlorobenzoyl chloride (0.098 mL, 0.5 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.25 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 10% (determined from NMR)

$^1$H NMR ($D_2O$): δ 0.88 (t, 3H, —$CH_2$—$CH_3$), δ 1.22-1.35 (m, 20H, (—$CH_2$—)$_{10}$), δ 1.60 (m, 2H, —$CH_2$—$CH_2$—CO—), δ 2.0 ppm (m, 4H, $(CH_2)_2$), δ 2.41 (t, 2H, —$CH_2$—CO—), δ 5.41 (d, 2H, CH═CH)

Example 10

Preparation of Oleyl (C18:1) Derivative of Hyaluronic Acid by Means of the Mixed Anhydride of 2,4,6-Trichlorobenzoic Acid and Oleic Acid 0.5 g of sodium hyaluronate (1.25 mmol, 130 kDa) were dissolved in 5 mL of demineralized water. Afterwards, 3 mL of isopropanol were gradually added. Then. TEA (0.52 mL, 3 eq.) and DMAP (15.0 mg, 0.1 eq.) were added to the solution. Simultaneously, oleic acid (0.4 mL, 1 eq.) was dissolved in 5 mL of isopropanol and then TEA (0.52 mL, 3 eq.) and 2,4,6-trichlorobenzoyl chloride (0.195 mL, 1 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.25 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 12% (determined from NMR)

$^1$H NMR ($D_2O$): δ 0.88 (t, 3H, —$CH_2$—$CH_3$), δ 1.22-1.35 (m, 20H, (—$CH_2$—)$_{10}$), δ 1.60 (m, 2H, —$CH_2$—$CH_2$—CO—), δ 2.0 ppm (m, 4H, $(CH_2)_2$), δ 2.41 (t, 2H, —$CH_2$—CO—), δ 5.41 (d, 2H, CH═CH)

Example 11

Preparation of Oleyl (C18:1) Derivative of Hyaluronic Acid by Means of the Mixed Anhydride of Isobutyryl Chloride and Oleic Acid 1.0 g of sodium hyaluronate (2.5 mmol, 15 kDa) were dissolved in 10 mL of demineralized water. Afterwards, 5 mL of THF were gradually added. Then, TEA (1.05 mL, 3 eq.) and DMAP (15.0 mg, 0.05 eq.) were added to the solution. Simultaneously, oleic acid (0.787 mL, 1 eq.) was dissolved in 5 mL of THF and then TEA (1.05 mL, 3 eq.) and isobutyryl chloride (0.26 mL, 1 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.50 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 11% (determined from NMR)

$^1$H NMR (D$_2$O): δ 0.88 (t, 3H, —CH$_2$—CH$_3$), δ 1.22-1.35 (m, 20H, (—CH$_2$—)$_{10}$), δ 1.60 (m, 2H, —CH$_2$—CH$_2$—CO—), δ 2.0 ppm (m, 4H, (CH$_2$)$_2$), δ 2.41 (t, 2H, —CH$_2$—CO—), δ 5.41 (d, 2H, CH=CH)

Example 12

Preparation of Oleyl (C18:1) Derivative of Hyaluronic Acid by Means of the Mixed Anhydride of 2,4,6-Trichlorobenzoic Acid and Oleic Acid 0.5 g of sodium hyaluronate (1.25 mmol, 130 kDa) were dissolved in 5 mL of demineralized water. Afterwards, 3 mL of THF were gradually added. Then, TEA (1.2 mL, 3 eq.) and DMAP (15.0 mg, 0.1 eq.) were added to the solution. Simultaneously, oleic acid (0.787 mL, 2 eq.) was dissolved in 10 mL of THF and then TEA (0.52 mL, 3 eq.) and 2,4,6-trichlorobenzoyl chloride (0.391 mL, 2 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.25 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 18% (determined from NMR)

$^1$H NMR (D$_2$O): δ0.88 (t, 3H, —CH$_2$—CH$_3$), δ 1.22-1.35 (m, 20H, (—CH$_2$—)$_{10}$) δ 1.60 (m, 2H, —CH$_2$—CH$_2$—CO—), δ 2.0 ppm (m, 4H, (CH$_2$)$_2$), δ 2.41 (t, 2H, —CH$_2$—CO—), δ 5.41 (d, 2H, CH=CH)

Example 13

Preparation of the Linoleyl (C18:2) Derivative of Hyaluronic Acid by Means of the Mixed Anhydride of 2,4,6-Trichlorobenzoic Acid and Linoleic Acid 0.5 g of sodium hyaluronate (1.25 mmol, 15 kDa) were dissolved in 10 mL of demineralized water. Then, TEA (0.52 mL, 3 eq.) and DMAP (8 mg, 0.05 eq.) were added to the solution. Simultaneously, linoleic acid (0.77 mL, 2 eq.) was dissolved in 3 mL of THF and then TEA (1.2 mL, 7 eq.) and 2,4,6-trichlorobenzoyl chloride (0.391 mL, 2 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.5 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 16% (determined from NMR)

$^1$H NMR (D$_2$O): δ 0.88 (t, 3H, —CH$_2$—CH$_3$), δ 1.22-1.35 (m, 14H, (—CH$_2$—)$_7$), δ 1.63 (m, 2H, —CH$_2$—CH$_2$—CO—), δ 2.0 ppm (m, 4H, (CH$_2$)$_2$), δ 2.44 (t, 2H, —CH$_2$—CO—), δ 2.83 (m, 2H, =CH—CH$_2$—CH=), δ 5.45 (m, 4H, CH=CH)

Example 14

Preparation of Linoleyl (C18:2) Derivative of Hyaluronic Acid by Means of the Mixed Anhydride of 2,4,6-Trichlorobenzoic Acid and Linoleic Acid 0.5 g of sodium hyaluronate (1.25 mmol, 15 kDa) were dissolved in 10 mL of demineralized water. Then, TEA (0.52 mL, 3 eq.) and DMAP (8 mg, 0.05 eq.) were added to the solution. Simultaneously, linoleic acid (0.77 mL, 2 eq.) was dissolved in 3 mL of THF and then TEA (1.2 mL, 7 eq.) and 2,4,6-trichlorobenzoyl chloride (0.391 mL, 2 eq.) were added to the solution. Following the activation of the acid, the precipitate was filtered into the prepared solution of HA. The reaction was taking place under room temperature for 3 hours and subsequently the reaction mixture was being warmed up at 50° C. for 1 hour. Afterwards, the reaction mixture was diluted with 5 mL of demineralized water containing the addition of 0.75 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 20% (determined from NMR)

$^1$H NMR (D$_2$O): δ 0.88 (t, 3H, —CH$_2$—CH$_3$), δ 1.22-1.35 (m, 14H, (—CH$_2$—)$_7$). δ 1.63 (m, 2H, —CH$_2$—CH$_2$—CO—), δ 2.0 ppm (m, 4H, (CH$_2$)$_2$), δ 2.44 (t, 2H, —CH$_2$—CO—), δ 2.83 (m, 2H, =CH—CH$_2$—CH=), δ 5.45 (m, 4H, CH=CH)

Example 15

Preparation of Linolenyl (C18:3) Derivative of Hyaluronic Acid by Means of the Mixed Anhydride of 2,4,6-Trichlorobenzoic Acid and Linolenic Acid 0.5 g of sodium hyaluronate (1.25 mmol, 15 kDa) were dissolved in 10 mL of demineralized water. Then, TEA (0.52 mL, 3 eq.) and DMAP (8 mg, 0.05 eq.) were added to the solution. Simultaneously, linolenic acid (0.765 mL, 2.0 eq.) was dissolved in 5 mL of THF and then TEA (0.52 mL, 3 eq.) and 2,4,6-trichlorobenzoyl chloride (0.391 mL, 2.0 eq.) were added to the solution. Following the activation of the acid, the precipitate was filtered into the prepared solution of HA. The reaction was taking place under room temperature for 3 hours. Afterwards, the reaction mixture was diluted with 5 mL of demineralized water containing the addition of 0.75 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 15% (determined from NMR)

$^1$H NMR (D$_2$O): δ 0.88 (t, 3H, —CH$_2$—CH$_3$), δ 1.22-1.35 (m, 8H, (—CH$_2$—)$_4$), δ 1.61 (m, 2H, —CH$_2$—CH$_2$—CO—), δ 2.0 ppm (m, 4H, (CH$_2$)$_2$), δ 2.43 (t, 2H, —CH$_2$—CO—), δ 2.83 (m, 4H, =CH—CH$_2$—CH=), δ 5.45 (m, 6H, CH=CH)

Example 16

Preparation of the Linolenyl (C18:3) Derivative of Hyaluronic Acid by Means of the Mixed Anhydride of 2,4,6-Trichlorobenzoic Acid and Linolenic Acid 0.5 g of sodium hyaluronate (1.25 mmol, 15 kDa) were dissolved in 10 mL of demineralized water. Then, TEA (0.52 mL, 3 eq.) and DMAP (8 mg, 0.05 eq.) were added to the solution. Simultaneously, linolenic acid (0.382 mL, 1 eq.) was dissolved in 5 mL of THF and then TEA (0.52 mL, 3 eq.) and 2,4,6-trichlorobenzoyl chloride (0.195 mL, 1 eq.) were added to the solution. Following the activation of the acid, the precipitate was filtered into the prepared solution of HA. The reaction was taking place under room temperature for 3 hours and subsequently the reaction mixture was being warmed up at 50° C. for 1 hour. Afterwards, the reaction mixture was diluted with 5 mL of demineralized water containing the addition of 0.25 g of NaCl. The acylated derivative was isolated from the reaction mixture in the subsequent precipitation process using the 4-fold of absolute isopropanol. After having undergone decantation, the precipitate was repeatedly washed initially with the aqueous solution of isopropanol (85% by vol.) in order to remove DMAP from the derivative and subsequently with absolute isopropanol in order to remove water from the derivative. Afterwards, the precipitate was being dried under the temperature of 40° C. for 48 hours and subsequently it was lyophilized for the purpose of removing the residual solvents.

DS 10% (determined from NMR)

$^1$H NMR (D$_2$O): δ 0.88 (t, 3H, —CH$_2$—CH$_3$), δ 1.22-1.35 (m, 8H, (—CH$_2$—)$_4$), δ 1.61 (m, 2H, —CH$_2$—CH$_2$—CO—), δ 2.0 ppm (m, 4H, (CH$_2$)$_2$), δ 2.43 (t, 2H, —CH$_2$—CO—), δ 2.83 (m, 4H, =CH—CH$_2$—CH=), δ 5.45 (m, 6H, CH=CH)

Example 17

Encapsulation of Tocopherol (Vitamin E) into the Capronyl (C6) Derivative of Hyaluronic Acid 100 mg of the acylated derivative of hyaluronan, which had been prepared according to Example 1, were being dissolved in 5 mL of water under continuous stirring for 3 hours. The resulting solution was gradually supplemented with the solution of tocopherol (10 mg in 3 mL of CHCl$_3$) under continuous stirring and under the temperature ranging between 25 and 40° C. and afterwards another 3 mL of CHCl$_3$ were gradually added. Subsequently, CHCl$_3$ was removed from the solution in a continuous evaporation process. Following the removal of CHCl$_3$, the aqueous phase was completely dried, rehydrated over an aqueous bath and filtered to an 1 μm glass filter. The filtrate was lyophilized.

The amount of bound tocopherol (determined by means of the HPLC method) was: 2.3% (w/w)

Example 18

Encapsulation of Nile Red into the Capronyl (C6) Derivative of Hyaluronic Acid 100 mg of the acylated derivative of hyaluronan, which had been prepared according to Example 1, were being dissolved in 5 mL of water under continuous stirring for 3 hours. The resulting solution was gradually supplemented with the solution of Nile red (10 mg in 3 mL of CHCl$_3$) under continuous stirring and under the temperature ranging between 25 and 40° C. and afterwards another 3 mL of CHCl$_3$ were gradually added. Subsequently. CHCl$_3$ was removed from the solution in a continuous evaporation process. Following the removal of CHCl$_3$, the aqueous phase was completely dried, rehydrated over an aqueous bath and filtered to an 1 μm glass filter. The filtrate was lyophilized.

The amount of bound Nile red (determined by means of the UV-Vis method) was: 0.4% (w/w)

Example 19

Encapsulation of Paclitaxel into the Capronyl (C6) Derivative of Hyaluronic Acid 100 mg of the acylated derivative of hyaluronan, which had been prepared according to Example 1. were being dissolved in 5 mL of water under continuous stirring for 3 hours. The resulting solution was gradually supplemented with the solution of paclitaxel (10 mg in 3 mL of CHCl$_3$) under continuous stirring and under the temperature ranging between 25 and 40° C. and afterwards another 3 mL of CHCl$_3$ were gradually added. Subsequently, CHCl$_3$ was removed from the solution in a continuous evaporation process. Following the removal of CHCl$_3$, the aqueous phase was completely dried, rehydrated over an aqueous bath and filtered to an 1 μm glass filter. The filtrate was lyophilized.

The amount of bound paclitaxel (determined by means of the HPLC method): 5% (w/w)

Example 20

Encapsulation of Phosphatidylcholine into Capronyl (C6) Derivative of Hyaluronic Acid 100 mg of the acylated derivative of hyaluronan, which had been prepared according to Example 1, were being dissolved in 5 mL of water under continuous stirring for 3 hours. The resulting solution was gradually (dropwise) supplemented with the solution of phosphatidylcholine (10 mg in 5 mL of EtOH) under continuous stirring. EtOH was removed from the solution in a continuous evaporation process. Subsequently, the residual aqueous phase was completely dried, rehydrated over an aqueous bath and filtered to an 1 μm glass filter. The filtrate was lyophilized.

The amount of bound phosphatidylcholine (determined by means of the HPLC method): 3.0% (w/w).

Example 21

Encapsulation of Coenzyme Q10 into Palmitoyl (C16) Derivative of Hyaluronic Acid 100 mg of the acylated derivative of hyaluronan, which had been prepared according to Example 7, were being dissolved in 10 mL of water under continuous stirring overnight. The resulting solution was gradually supplemented with the solution coenzyme Q10 (20 mg in 5 mL of $CHCl_3$) under continuous stirring and under the temperature ranging between 30 and 40° C. and afterwards another 3 mL of $CHCl_3$ were gradually added. Subsequently, $CHCl_3$ was removed from the solution in a continuous evaporation process. Following the removal of $CHCl_3$, the aqueous phase was completely dried, rehydrated over an aqueous bath and filtered to an 1 μm glass filter. The filtrate was lyophilized.

The amount of bound coenzyme Q10 (determined by means of the UV-Vis method) was: 12% (w/w)

When the product is dissolved in the 0.9% solution of NaCl, a coacervate or gel-like solution is formed in dependence on the concentration of the dissolved product.

Example 22

Encapsulation of Tocopherol (Vitamin E) into Stearyl (C18) Derivative of Hyaluronic Acid 100 mg of the acylated derivative of hyaluronan, which had been prepared according to Example 8, were being dissolved in 10 mL of water under continuous stirring overnight. The resulting solution was gradually supplemented with the solution of tocopherol (about 50 mg in 5 mL of ethanol) under continuous stirring and under the temperature ranging between 25 and 40° C. Subsequently, ethanol was removed from the solution in a continuous evaporation process. Following the removal of EtOH, the aqueous phase was completely dried, rehydrated over an aqueous bath and filtered to an 1 μm glass filter. The filtrate was lyophilized.

The amount of bound tocopherol (determined by means of the UV-Vis method) was: 30% (w/w)

Example 23

Encapsulation of Tocopherol (Vitamin E) into Oleyl (C18:1) Derivative of Hyaluronic Acid 100 mg of the acylated derivative of hyaluronan, which had been prepared according to Example 9, were being dissolved in 10 mL of water under continuous stirring overnight. The resulting solution was gradually supplemented with the solution of tocopherol (about 50 mg in 5 mL of isopropanol) under continuous stirring and under the temperature ranging between 25 and 40° C. Subsequently, isopropanol was removed from the solution in a continuous evaporation process. Following the removal of isopropanol, the aqueous phase was completely dried, rehydrated over an aqueous bath and filtered to an 1 μm glass filter. The filtrate was lyophilized.

The amount of bound tocopherol (determined by means of the UV-Vis method) was: 40% (w/w)

Example 24

Encapsulation of Coenzyme Q10 into Palmitoyl (C16) Derivative of Hyaluronic Acid 100 mg of the acylated derivative of hyaluronan. which had been prepared according to Example 7, were being dissolved in 10 mL of water under continuous stirring overnight. The resulting, solution was gradually supplemented with the solution of coenzyme Q10 (about 30 mg in 2 mL of EtOH) under continuous stirring. After having been stirred for 3 hours, the resulting mixture was being subject to sonication (100 W) for 30 minutes. Subsequently, the mixture underwent intensive dialysis (for 2 days) against distilled water and it was filtered through a 1 μm glass filter and lyophilized.

The amount of bound coenzyme Q10 (determined by means of the UV-Vis method) was: 4.6% (w/w)

When the product is dissolved in the 0.9% solution of NaCl, a coacervate or gel-like solution is formed in dependence on the concentration of the dissolved product.

Example 25

Encapsulation of Paclitaxel into the Palmitoyl (C16) Derivative of Hyaluronic Acid 100 mg of the acylated derivative of hyaluronan, which had been prepared according to Example 7, were being dissolved in 10 mL of water under continuous stirring overnight. The resulting solution was gradually supplemented with the solution of paclitaxel Q10 (about 40 mg in 2 mL of EtOH) under continuous stirring. After having been stirred for 3 hours, the resulting mixture was being subject to sonication (100 W) for 30 minutes. Subsequently, the mixture underwent intensive dialysis (3.5 kDa cut off) against distilled water and it was filtered through an S4 porcelain frit and lyophilized.

The amount of bound paclitaxel (determined by means of the HPLC method): 25% (w/w)

Example 26

Encapsulation of Hop Extract into oleyl (C18:1) Derivative of Hyaluronic Acid 100 mg of the acylated derivative of hyaluronan, which had been prepared according to Example 9, were being dissolved in 10 mL of water under continuous stirring overnight. The resulting solution was gradually supplemented with the solution of a hop extract blend (about 50 mg in 5 mL of isopropanol) under continuous stirring. Subsequently, isopropanol was removed from the solution in a continuous evaporation process. Following the removal of isopropanol, the aqueous phase was completely dried, rehydrated over an aqueous bath and filtered to an 1 μm glass filter. The filtrate was lyophilized.

The amount of bound tocopherol (determined by means of the UV-Vis method) was: 40% (w/w)

Example 27

Determination of the Critical Micellar (Aggregation) Concentrations of Acylated Derivatives of Hyaluronic Acid (a) Fluorescence Method The critical micellar (aggregation) concentration was determined from the dependence of the fluorescence intensity on the solution concentrations (FIG. 1). The emission spectra (580-700 nm) of the aqueous solutions of the acylated derivatives HAC6 (DS=60%) and HAC16 (DS=14%) with bound Nile red, which had been prepared in the concentration range from 0.00002 to 1.5 mg·mL$^{-1}$ in accordance with the procedure described in example 18, were measured in the fluorometric apparatus RF-5301 (Shimadzu) working with the excitation wavelength of 543 nm.

The following critical micellar (aggregation) concentrations were determined: for HA C6: 0.001-0.003 mg·mL$^{-1}$, for HA C16: 0.00006-0.0002 mg·mL$^{-1}$ (FIG. 1). The same measurement value was obtained for PBS with the 0.9% NaCl solution.

(b) Static Light Scattering Method

Figure 2:
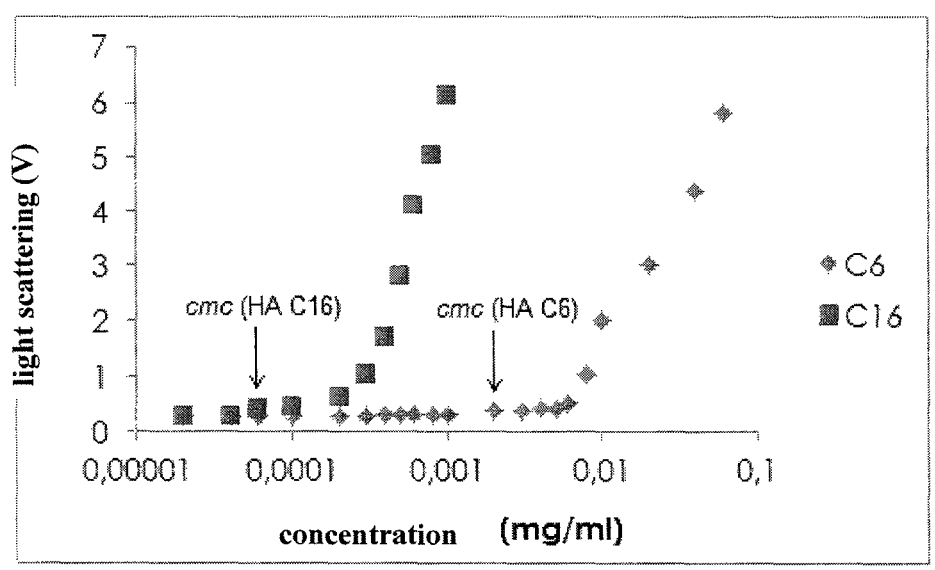
FIG. 2. Determination of the critical micellar (aggregation) concentration (CMC) using the static light scattering method on the acylated hyaluronan derivative (C6) and (C16) with encapsulated oil red in water.

The critical micellar (aggregation) concentration was determined from the dependence of the intensities of scattered light ($I_{90}$) on the solution concentrations (FIG. 2). The intensity of the scattered light in the aqueous solutions of the acylated derivatives HAC6 (DS=60%) and HAC16 (DS=14%) with bound Nile red, which had been prepared in the concentration range from 0.00002 to 0.06 mg·mL$^{-1}$ in accordance with the procedure described in example 18, were measured at the angle of 90° in the photometric apparatus DAWN EOS (Wyatt Technology Corporation) working with the wavelength of 632 nm.

The following critical micellar (aggregation) concentrations were determined: for HA C6: 0.002-0.004 mg·mL$^{-1}$, for HA C16: 0.00006-0.0001 mg·mL$^{-1}$ (FIG. 2). The same measurement value was obtained for PBS with the 0.9% NaCl solution.

Example 28

Determination of the Zeta Potential of Hyaluronan Nanomicelles

The zeta potential was determined in the apparatus Zetasizer Nano-ZS (Malvern Instruments) equipped with a He—Ne laser (633 nm). Independently on the encapsulated substance, the zeta potential exhibited by the nanomicelles in aqueous solutions was ~−50 mV at 5 mg·mL$^{-1}$ and from ~−60 to −70 mV after a 10-fold dilution. In the 0.9% solution of NaCl, the zeta potential range was reduced (−30 to −23 mV). Thus, the absolute value of the zeta potential indicates a high stability of the prepared nanomicelles in aqueous solutions and a relatively high stability of the same in salt solutions.

Example 29

Morphological Analysis of Hyaluronan Nanomicelles

The microscopic analyses were carried out at −135° C. in the scanning microscope JEOL 7401F working with the beam accelerating voltage of 2 kV (i.e. in a fine beam mode). For the purpose of the above analyzes, 2-3 μL of a concentrated sample (about 20 mg/0.4 mL) were dripped onto am Al plate and immersed into liquid nitrogen filled in the cryochamber Alta 2500 (Gatan). Subsequently, they were being coated with the Pt/Pd mixture for 2 minutes.

Figure 3:
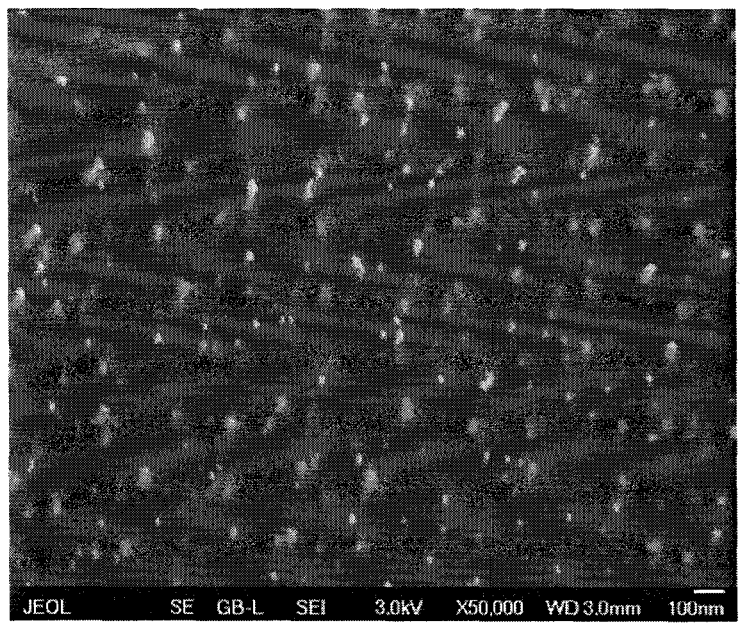
FIG. 3. Cry-SEM images of hyaluronan nanomicelles with encapsulated vitamin E (upper image) and with encapsulated paclitaxel (lower image).
Figure 3:
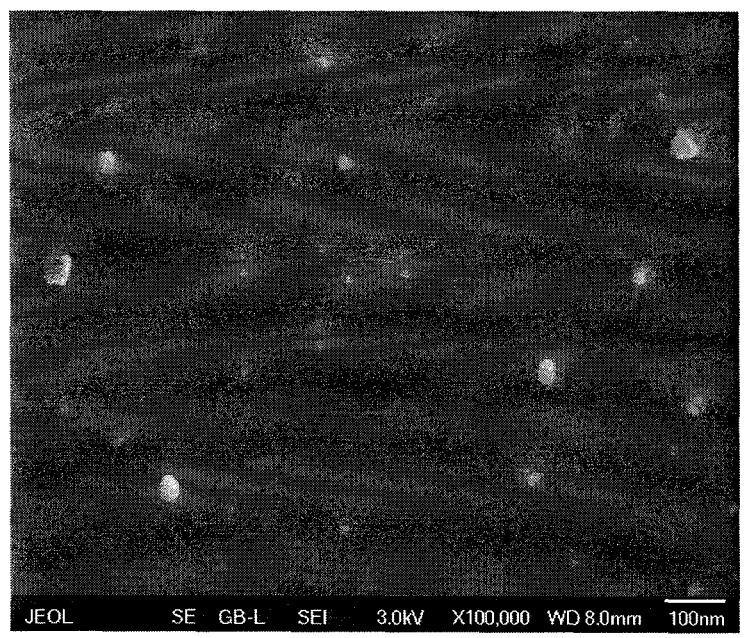

The size of nanomicelles of hyaluronan C6 with encapsulated vitamin E (Example 17) and hyaluronan C16 with encapsulated paclitaxel (example 25) was in the range: 20-50 nm (FIG. 3).

Example 30

Distribution of Acylated Chains and Nonpolar Substances in Hyaluronan Nanomicelles The separation of the nanomicelles of hydrophobized hyaluronan with encapsulated vitamin E was carried out by means of the flow field-flow fractionation (FIFFF) method using a frit-inlet separation channel. For the purpose of the analysis, 10 mg of lyophilized acylated hyaluronan with bound vitamin E (prepared from the derivatives listed in Table 1 in accordance with the procedure described in Example 23) were dissolved in 1 mL of the mobile phase (50 mM NaNO$_3$ with 0.02% NaN$_3$) and filtered through a glass syringe filter with 1 μm pore size. Subsequently, 100 μl were injected into the FIFFF apparatus.

The separation was carried out by means of the cross-flow gradient from 2 mL/min to 0.1 mL/min during a 5 minute interval. The flowrate of the mobile phase fed into the detector was kept constant, the setpoint being 1 mL/min.

The separation took place under laboratory temperature. The eluate was monitored by means of the light scattering detector DAWN EOS, the differential refractometer Optilab rEX (both made by the Wyatt Technology Corporation) and the UV detector working with the wavelength of 292 nm (Shimadzu).

When applying the above method, it is possible to determine both the percentage of the bound substance and hydrophobized hyaluronan firmly incorporated inside the nanomicelles and the percentage of the same present outside the aggregated structures (see Table 1).

TABLE 1

Distribution of acylated chains and vitamin E (tocopherol) inside and outside the hyaluronan aggregates (nanomicelles)

| Carrier (degree of substitution) | Bonding capacity of tocopherol (w/w %) | Non-aggregated acylated groups (%) | Aggregated acylated groups (%) | Free vitamin E (%) | Bound vitamin E (%) |
|---|---|---|---|---|---|
| HAC6 (DS = 55%) | 6.9 | 91.5 | 8.5 | 0.5 | 99.5 |
| HAC8 (DS = 15%) | 12.4 | 82.1 | 17.9 | 0.4 | 99.6 |

TABLE 1-continued

Distribution of acylated chains and vitamin E (tocopherol) inside and outside the hyaluronan aggregates (nanomicelles)

| Carrier (degree of substitution) | Bonding capacity of tocopherol (w/w %) | Non-aggregated acylated groups (%) | Aggregated acylated groups (%) | Free vitamin E (%) | Bound vitamin E (%) |
|---|---|---|---|---|---|
| HAC10 (DS = 15%) | 18.5 | 47.2 | 52.8 | 0.5 | 99.5 |
| HAC18 (DS = 10%) | 40 | 21.5 | 78.5 | 0.3 | 99.7 |

The results listed in Table 1 clearly show that the distribution of the acylated chains in the hyaluronan nanomicelles is primarily influenced by the length of an acyl chain. The degree of aggregation of acyl chains increases with the increasing length of the same. The incorporation of a nonpolar substance into a nanomicelle takes place independently on the length of the respective acyl chain. In this particular case, the distribution of a nonpolar substance in a micelle always entirely prevails (>99.5%).

Example 31

Cytotoxicity of Nanomicelles Carrying a Paclitaxel Based Cytostatic Drug

Figure 4:
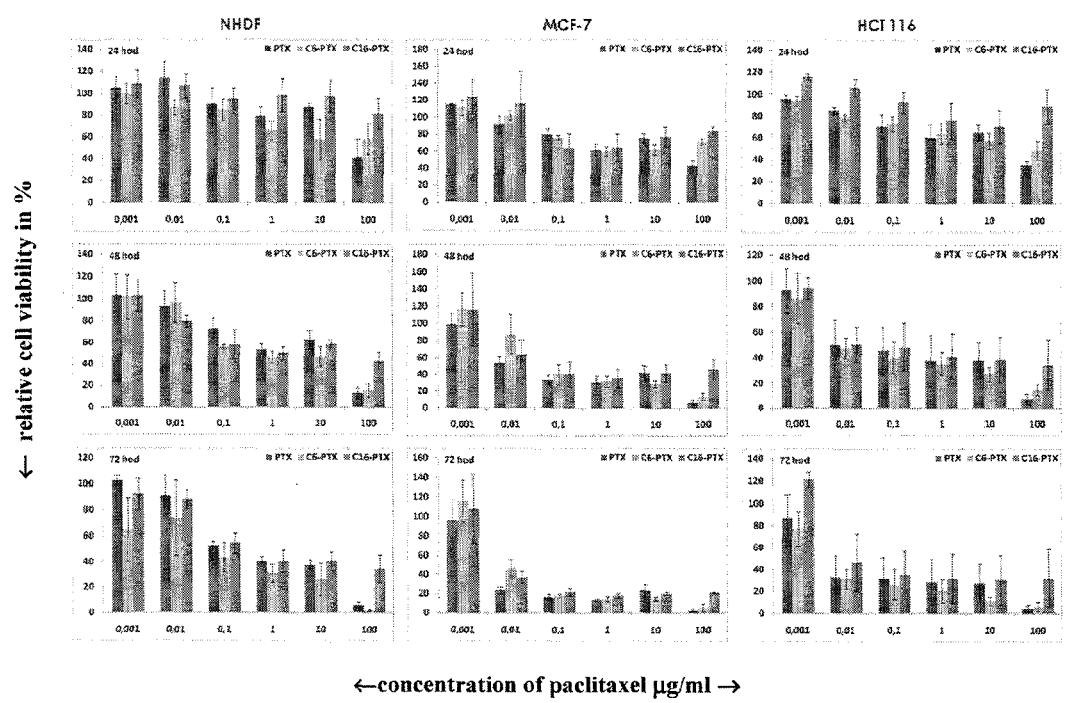
FIG. 4. Cytotoxicity of paclitaxel and of paclitaxel encapsulated in HAC6 and HAC16 in dependence on the concentration and on the time of cellular interaction.

Paclitaxel linked to the acylated derivatives of hyaluronan C6 and C16, which had been prepared in accordance with the procedures described in examples 19 and 25 respectively, was dissolved in a cultivating medium (containing 10% of FBS), the final concentration being 100 µg/mL. Cells of human dermal fibroblasts (NHDF), a cell line of human breast carcinoma (MCF-7) and a cell line of human colon carcinoma (HCT 116) were used for testing the paclitaxel concentrations of 0.001, 0.01, 0.1, 1.0, 10.0 and 100.0 µg/mL carried by the derivatives of acylated hyaluronan C6 and C16, the test being based on the measurements of the cell viability. The effect of paclitaxel carried by the derivatives of acylated hyaluronan C6 and C16 was the compared to that of paclitaxel on its own (FIG. 4). The measurement of cell viability is based on the detection of the activity of the dehydrogenase enzyme, which is active in live cells and transforms the yellow substrate into a violet solution. The absorbance of the latter, which is detected at 540 nm, is proportional to the percentage of live cells.

The increasing concentration of the carrier caused, particularly when HAC16 was used, a slight reduction of the cytostatic effectiveness of paclitaxel (FIG. 4).

The acylated derivatives themselves did not exhibit any cytostatic effects.

Example 32

Transfer of Encapsulated Substances into Cells

Figure 5:
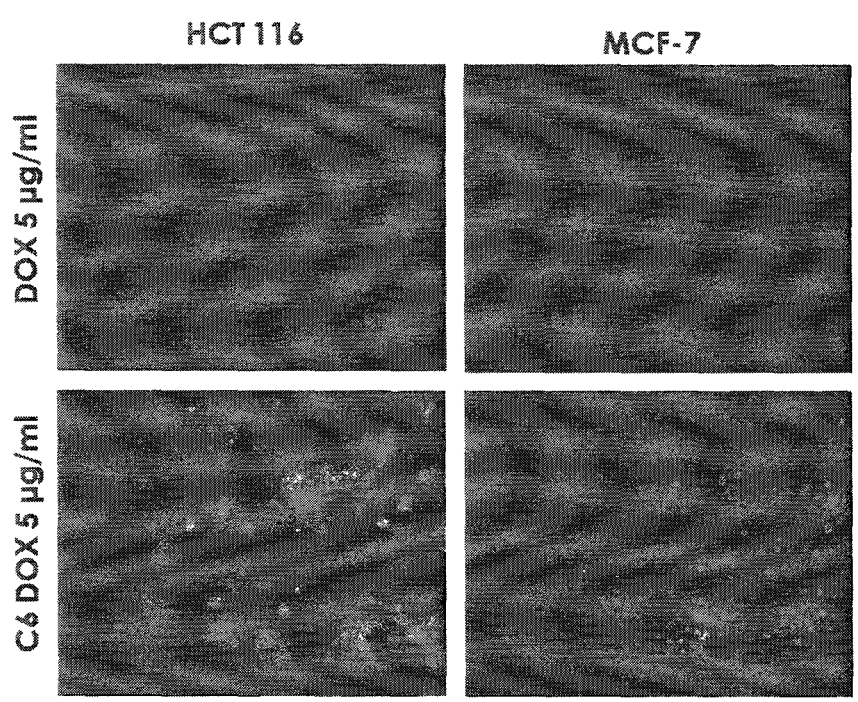
FIG. 5. Transport of doxorubicin into HCT 116 and MCF-7 cells after 1 hour of exposure.
Figure 6:
FIG. 6. Cellular internalization with 7AAD in live cells using HA(C6) carriers with encapsulated 7AAD.

The substances doxorubicin and 7-aminoactinomycin D (7-AAD, which is as substance that only penetrates into dead and permeabilized cells) were encapsulated into the acylated derivative of hyaluronan C6 in accordance with the procedure described in example 18 (where 7-AAD was substituted for Nile red). Cells of human dermal fibroblasts (NHDF), a cell line of human breast carcinoma (MCF-7) and a cell line of human colon carcinoma (HCT 116) were used for testing the existence of a difference between the penetration of an substance into a cell when the substance is applied in a solution, in which it is present on its own) or in an acylated derivative of hyaluronan C6. The tests were carried out by means of the fluorescence microscopy method (inverted microscope Nikon Eclipse Ti). Doxorubicin was tested in the concentration of 5.0 µg/mL (FIG. 5) and 7-AAD was tested in the concentration of 15 µg/mL (FIG. 6).

The transfer of the substances from the carrier into the cells was successful.

Example 33

Release of Encapsulated Oil Red from Nanomicelles into a Solution

Figure 7:
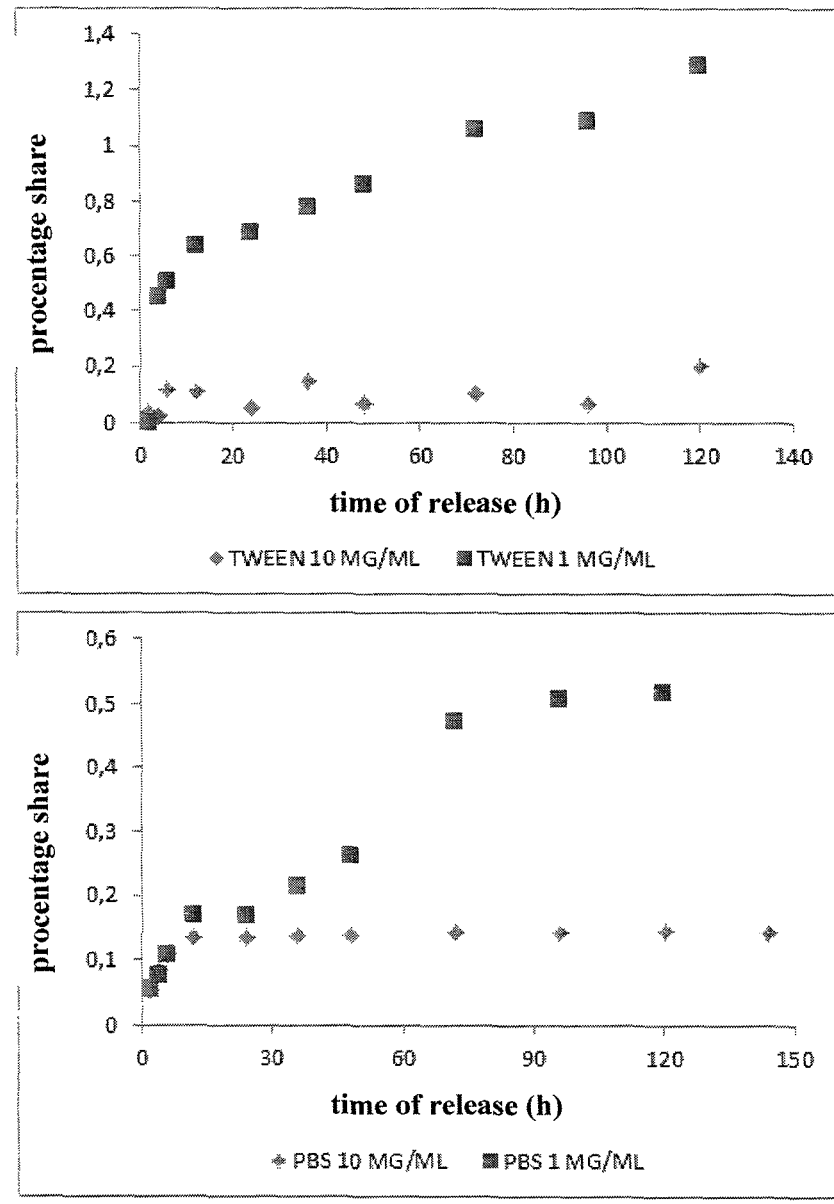
FIG. 7. Profile of the release of encapsulated oil red from the HAC6 carrier into PBS and into PBS containing 1% of added TWEEN 80. Concentration of HAC6+oil red: 1 or 10 mg·mL$^{-1}$.

The release of oil red (Oil Red 0, solvent red 27) encapsulated in HAC6 in accordance with the procedure described in example 18 (where Oil Red 0 was substituted for Nile red) into solutions was studied in vitro. The target solutions used were PBS and PBS with the addition of 1% of TWEEN 80. The aqueous solutions of acylated derivatives with bound oil red (in the concentration range between 1 and 10 mg·mL$^{-1}$) were dissolved in PBS or in PBS with the addition of 1% of TWEEN 80, quantitatively transferred into the dialysis tubing (MWCO 12-14 kDa, Spectrum Laboratories) and dialysed under the temperature of 37° C. against PBS or against PBS with the addition of 1% of TWEEN 80. In predefined time intervals, 4 mL of the dialysate were being sampled and replaced with a fresh medium. The released amount of oil red was determined by means of the UV-Vis method (FIG. 7).

The slow release of the bound substance is indicative of a high stability of carrier systems in PBS.

Example 34

Release of Encapsulated Paclitaxel from Nanomicelles into a Solution

Figure 8:
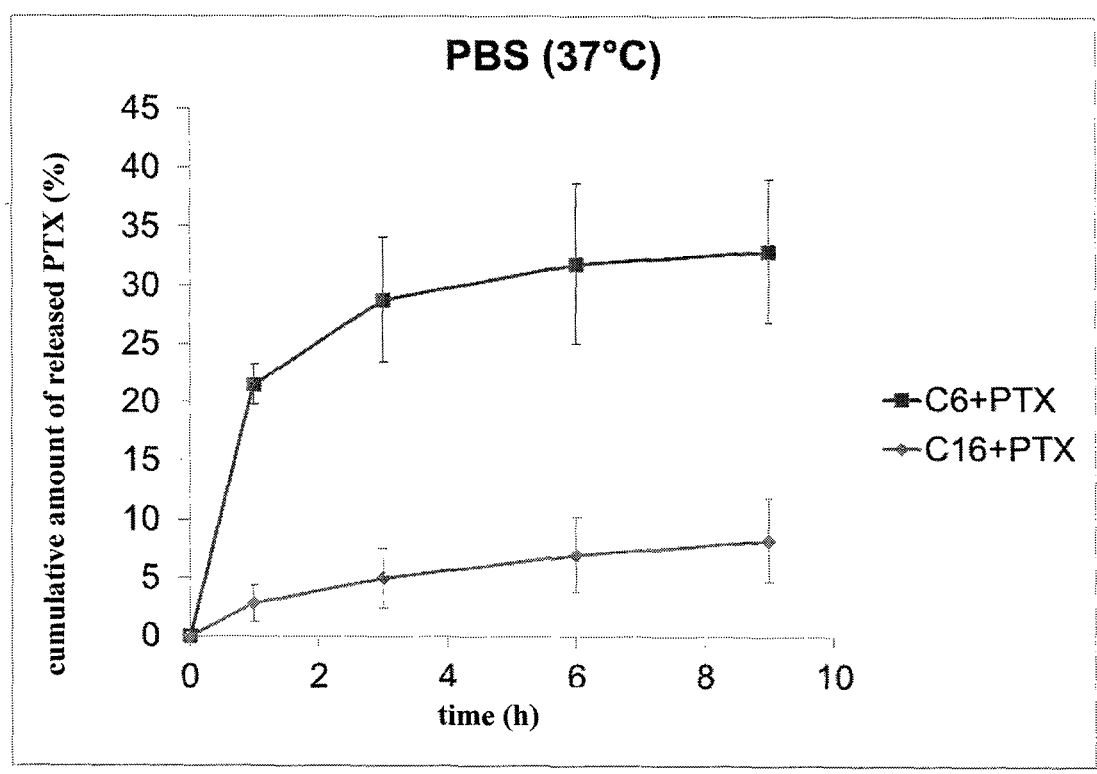
FIG. 8. Profile of the release of encapsulated paclitaxel from the HAC6 and HAC16 (c=10 mg·mL$^{-1}$) carriers into PBS.

The release of paclitaxel encapsulated in HAC6 and HAC16 in accordance with the procedure described in example 19 and 25 respectively into a solution was studied in vitro under the temperature of 37° C. The aqueous solutions of acylated derivatives containing paclitaxel in the total concentration of 0.2 mg were dissolved in PBS, quantitatively transferred into the dialysis tubing (MWCO 12-14 kDa, Spectrum Laboratories) and dialysed under the temperature of 37° C. against 50 mL of PBS. In predefined time intervals, the dialysate was being replaced with a fresh medium. The released amount of paclitaxel was determined after subjecting the same to the extraction into chloroform, evaporation and subsequent dissolution in acetonitrile by means of HPLC (FIG. 8).

The release registered for HAC16 was slower in comparison to HAC6. The slow release of the bound substance is indicative of a high stability of carrier systems in PBS.

Example 35

Preparation of Nanoemulsions and Microemulsions from the Oleyl Derivative (C18:1) of Hyaluronic and Oleic Acids 80 mg of the acylated derivative of hyaluronan, which had been prepared according to Example 11, were being dissolved in 4 mL of water under continuous stirring overnight. The resulting solution was gradually supplemented with the 8 mg of oleic acid under continuous stirring. After having been stirred, the resulting mixture was subject to two-step sonication (Ultrasonic Processor, UPS 200S, 200 W output). The first step, which was a continuous one (50% amplitude) was followed by the second step, which was a pulsation one (0.8 s pulses, 70% amplitude), each step lasting 25 minutes. During the sonication process, the receptacle containing the mixture being processed was immersed into ice bath in order to be protected from overheating.

Particle size (determined in Zetasizer): 200-300 nm. The size was dependent on the amount of oil phase in the mixture.

Example 36

Preparation of Nanoemulsions and Microemulsions from the Oleyl Derivative (C18:1) of Hyaluronic and Oleic Acids with Dissolved Coenzyme Q10

80 mg of the acylated derivative of hyaluronan, which had been prepared according to Example 11, were being dissolved in 4 mL of water under continuous stirring overnight. The resulting solution was gradually supplemented with the 8 mg of oleic acid containing coenzyme Q10 already dissolved therein (about 0.5 mg) under continuous stirring. After having been stirred, the resulting mixture was subject to two-step sonication (Ultrasonic Processor, UPS 200S, 200 W output). The first step, which was a continuous one (50% amplitude) was followed by the second step, which was a pulsation one (0.8 s pulses, 70% amplitude), each step lasting 25 minutes. During the sonication process, the receptacle containing the mixture being processed was immersed into ice bath in order to be protected from overheating.

Particle size (determined in Zetasizer): 200-300 nm. The size was dependent on the amount of oil phase in the mixture.

Example 37

Preparation of Stabilized Nanomicelles Through Covalent Cross-Linking 10 g of sodium hyaluronate (25 mmol, 38 kDa) were dissolved in 200 mL of demineralized water. Then, TEA (6.97 mL, 2 eq. relative to a dimer of HA) and DMAP (153 mg, 0.05 eq.) were added to the solution. Activation: 3.5 g of 3-(2-furyl)acrylic acid (25 mmol) were dissolved in 50 mL of tetrahydrofuran and 19.2 mL of TEA (2 eq.). Subsequently, the resulting solution was cooled down in an ice bath and supplemented with trichlorobenzoyl chloride (1.2 mL). The reaction was taking place for 15 minutes. Afterwards, the activated acid was added to the hyaluronan solution and the reaction was taking place under the temperature of 25° C. for 24 hours. The resulting reaction mixture was diluted with eater. The acrylated derivative was isolated from the reaction mixture in the subsequent precipitation process using the 4-fold of absolute isopropanol. After having undergone decantation, the precipitate was repeatedly washed with the aqueous solution of isopropanol (85% by vol.). Afterwards, the precipitate was being dried under the temperature of 40° C. for 48 hours. The obtained acrylated derivative was acylated (see example 1) and subsequently dissolved in water and lyophilized for the purpose of removing the residual solvents.

The carrier system, which had been prepared from oil red (Oil red 0) and from the acrylated derivative according to Example 18 (where oil red was substituted for Nile red), was dissolved to form an 1% aqueous solution. In the resulting solution, the carrier system was cross-linked by means of ammonium peroxydisulfate (10 eq.) used as trigger.

DS 20% of the active group for photo cross-linking (determined from NMR)

$^1$H NMR (D$_2$O): δ 7.83, 6.87 (d, J=3.5), 6.87, 6.61 (bs), 7.83, 7.59 (J$_{trans}$=16.01), 6.39 (J$_{trans}$=15.85).

Example 38

Figure 9:
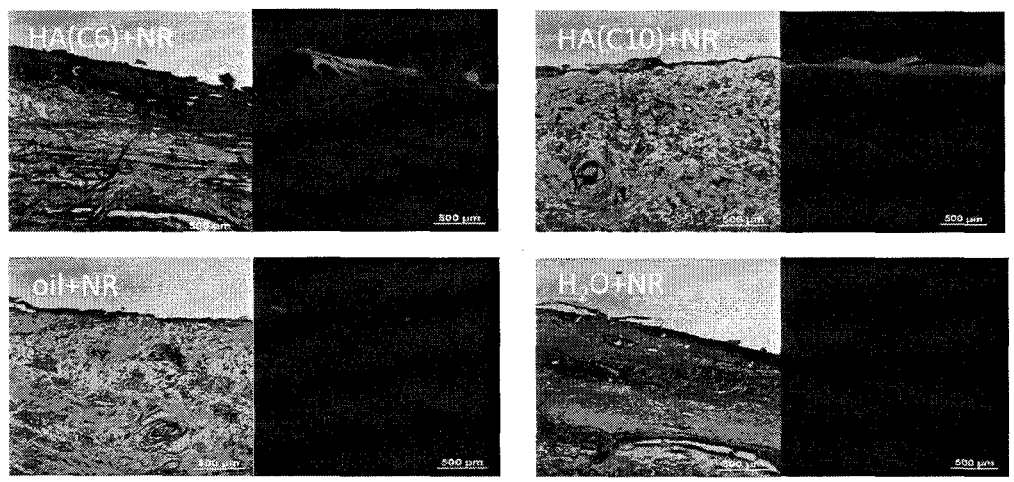
FIG. 9. Penetration of encapsulated Nile red (NR) from hyaluronan nanomicelles HA(C6) and HA (C10) vs. penetration of Nile red dissolved in oil and dispersed in water into skin, either Nile red sample having the same concentration.
Figure 10:
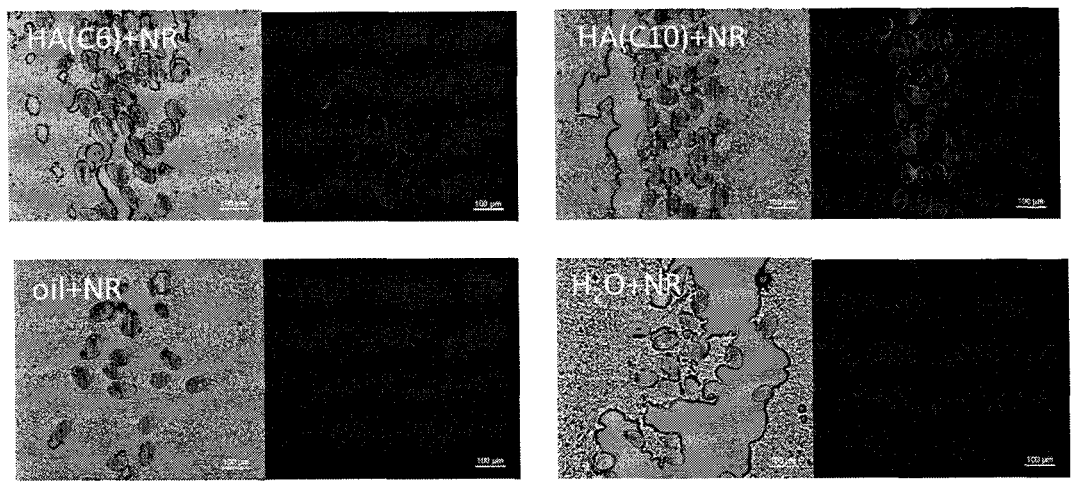
FIG. 10. Penetration of encapsulated Nile red (NR) from hyaluronan nanomicelles HA(C6) and HA (C10) vs. penetration of Nile red dissolved in oil and dispersed in water into hair, either Nile red sample having the same concentration (the microscopic image shows a cross section of a hair strand).
Figure 11:
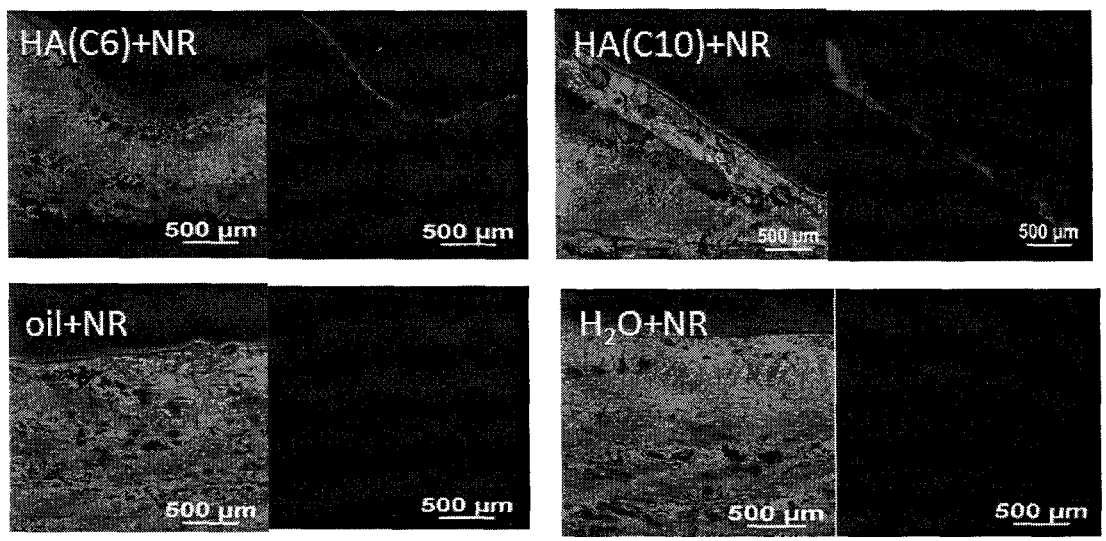
FIG. 11. Penetration of encapsulated Nile red (NR) from polymeric hyaluronan nanomicelles HA(C6) and HA (C10) vs. penetration of Nile red dissolved in oil and dispersed in water into buccal mucous membrane, either Nile red sample having the same concentration.
Figure 12:
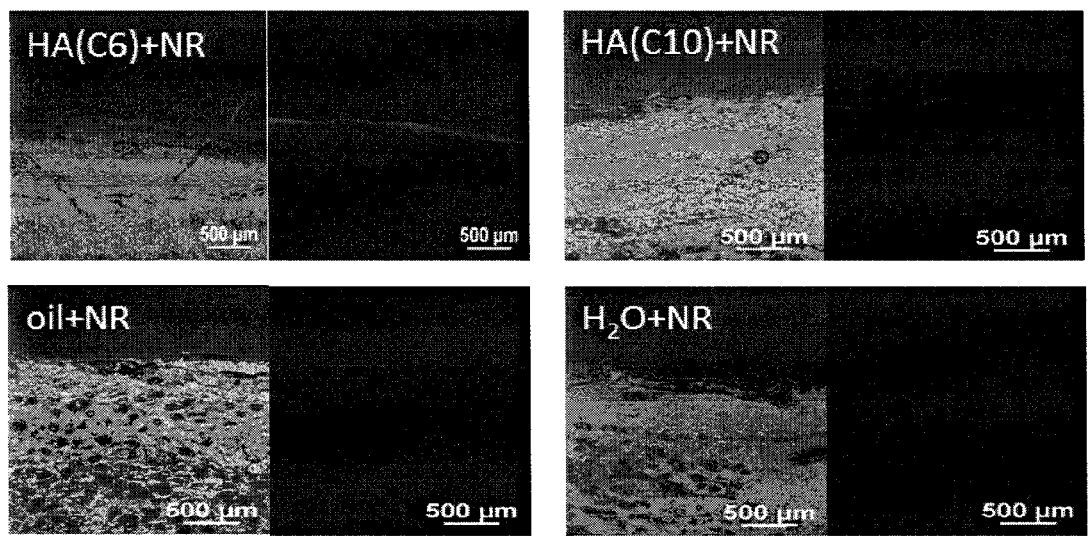
FIG. 12. Penetration of encapsulated Nile red (NR) from polymeric hyaluronan nanomicelles HA(C6) and HA (C10) vs. penetration of Nile red dissolved in oil and dispersed in water into a vaginal mucous membrane, either Nile red sample having the same concentration.

Topical Application of Hyaluronan Nanomicelles—Penetration into Skin, Hairs and Mucous Membranes Swine skin, bovine vaginal mucous membrane and bovine buccal mucous membrane were donated by the company MasoEko, s.r.o., based in Kunčice 243, Letohrad. Immediately after having been taken. the samples were subject to the passive action of the solution of acylated hyaluronan C6 and C10 (10 mg·mL$^{-1}$) with encapsulated Nile red (prepared in accordance with the procedure described in example 18) and the penetration into the samples was compared by measuring the fluorescence values in the inverted microscope Nikon Eclipse Ti (equipped with the objective lens Plan Fluor 4x). Subsequent incubation under the temperature of 37° C.: skin samples for 20 hours (FIG. 9), hair samples for 15 minutes (FIG. 10) and samples of mucous membranes for 4 hour (FIGS. 11 and 12).

The carriers have enabled a more efficient penetration into skin, hairs and mucous membranes to be achieved when compared with oil and aqueous solvents.

The invention claimed is:

1. Nanomicellar composition on the basis of a C$_6$-C$_{18}$-acylated derivative of hyaluronic acid according to the general formula (I):

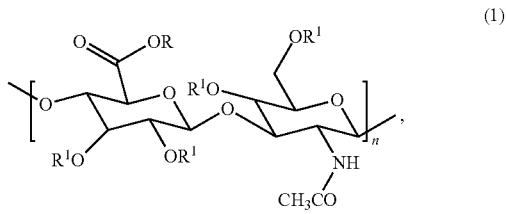

wherein R is H+ or Na$^+$ and R$^1$ is H or —C(=O)C$_x$H$_y$ or —C(=O)CH=CH-het, wherein x is an integer in a range of 5 to 17 and y is an integer in a range of 11 to 35 and CxHy is a linear or branched, saturated or unsaturated C$_5$-C$_{17}$ chain and het is a heterocyclic or heteroaromatic group having a selectable content of N, S or O atoms, at least one repeating unit containing one or more R$^1$ —C(=O)C$_x$H$_y$ or —C(=O)CH=CH-het groups, and wherein n is in a range of 12 to 4000; characterized in that the composition contains nanomicelles which comprise a hydrophobic core formed by the C$_6$-C$_{18}$-acyl groups linked to hyaluronic acid and a hydrophilic shell formed by the hydrophilic functional groups of hyaluronic acid and one or more biologically active substances being physically bounded in the nanomicelle.

2. Nanomicellar composition according to claim 1, characterized in that it contains 0.3 to 50% by weight of a biologically active substance relative to the mass content of the C$_6$-C$_{18}$-acylated derivative of hyaluronic acid, the biologically active substance being chosen from pharmaceutically and cosmetically active substances, vitamins, medicines, cytostatics, phytoextracts, phytocomplexes, phytoactive substances, mineral oils, vegetable oils, and mixtures thereof.

3. Nanomicellar composition according to claim 2, characterized in that the biologically active substance is tocoferol, paclitaxel, phosphatidylcholine or coenzyme Q10.

4. Nanomicellar composition according to claim 1, characterized in that it contains a $C_6$-$C_{18}$-acylated derivative of hyaluronic acid in a concentration which is in excess of its critical aggregation concentration.

5. Nanomicellar composition according to claim 1, characterized in that the concentration of the $C_6$-$C_{18}$-acylated derivative of hyaluronic acid is in a range of 0.0001 mg·mL$^{-1}$ to 30 mg·mL$^{-1}$ when the composition is in an aqueous solution.

6. Nanomicellar composition according to claim 1, characterized in that the biologically active substance is a mineral or vegetable oil in the amount of 0.05 to 40% by weight relative to the mass content of the $C_6$-$C_{18}$-acylated derivative of hyaluronic acid.

7. Nanomicellar composition according to claim 1, characterized in that it contains a biologically active substance which is liquid and insoluble in water, said substance containing an additional biologically active substance dissolved therein.

8. Nanomicellar composition according to claim 7, characterized in that the biologically active substance, which is liquid and insoluble in water, is a mineral or vegetable oil, and the additional biologically active substance is selected from the group consisting of pharmaceutically or cosmetically active substances.

9. Nanomicellar composition according to claim 1, characterized in that it is in the form of a solution, nanoemulsion, microemulsion, coacervate or gel.

10. Method of preparation of the nanomicellar composition according to claim 1, characterized in that the $C_6$-$C_{18}$-acylated derivative of hyaluronic acid according to the general formula (I) is dissolved in water, the biologically active substance is dissolved in an organic solvent, the resulting solutions are mixed together and afterwards the organic solvent is removed.

11. Method of preparation according to claim 10, characterized in that the organic solvent is removed by vacuum evaporation, subsequently the aqueous phase is dried and rehydrated and the resulting nanomicellar structures are filtered and finally lyophilized.

12. Method of preparation according to claim 10, characterized in that the organic solvent is removed by dialysis, subsequently the resulting nanomicellar structures are filtered and finally lyophilized.

13. Method of preparation according to claim 10, characterized in that the organic solvent is a volatile chlorinated solvent or an alcohol.

14. Method of preparation of the nanomicellar composition defined in claim 1, characterized in that the $C_6$-$C_{18}$-acylated derivative of hyaluronic acid according to the general formula (I) is dissolved in water and subsequently mixed together with a biologically active substance, which is liquid and insoluble in water, whereupon the resulting mixture is homogenized by sonication to form a microemulsion or nanoemulsion.

15. Method of preparation of the nanomicellar composition defined in claim 7, characterized in that the $C_6$-$C_{18}$-acylated derivative of hyaluronic acid according to the general formula (I) is dissolved in water and subsequently mixed together with a biologically active substance, which is liquid and insoluble in water and in which an additional biologically active substance is dissolved, whereupon the resulting mixture is homogenized by sonication to form a microemulsion or nanoemulsion.

16. Method of preparation of a stabilized nanomicellar composition, characterized in that a $C_6$-$C_{18}$-acylated hyaluronan according to the general formula (II) is prepared:

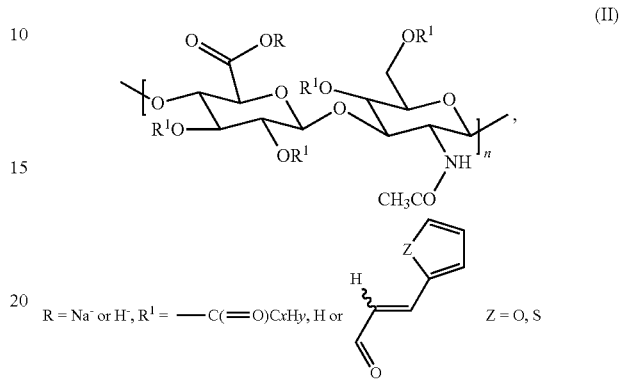

wherein n is in a range of 12 to 4000, R represents H$^+$ or Na$^+$, and one or more R$^1$ members are represented by (i) a linear $C_6$-$C_{18}$-chain corresponding to the formula —C(=O)$C_xH_y$ in at least one repeating unit wherein x is an integer in a range of 5 to 17 and y is an integer in a range of 11 to 35, which linear chain can contain unsaturated bonds, (ii) 3-(2-thienyl)acrylic acid, or (iii) 3-(2-furyl)acrylic acid in at least one repeating unit, whereupon a nanomicellar composition is prepared from the $C_6$-$C_{18}$-acylated hyaluronan according to the general formula (II), which composition is then stabilized in a cross-linking reaction.

17. Method of preparation according to claim 16, characterized in that first hyaluronic reacts with 3-(2-thienyl)acrylic acid or 3-(2-furyl)acrylic acid under the presence of a base and a catalyst in a mixture of water and a water-miscible aprotic solvent, said acids being activated with a chloride of 2,4,6-trichlorobenzoic acid or an organic chloride of R$_3$—CO—Cl, wherein R$_3$ is a linear or branched $C_1$-$C_{30}$-alkyl, to form an acrylated hyaluronan according to the formula (III):

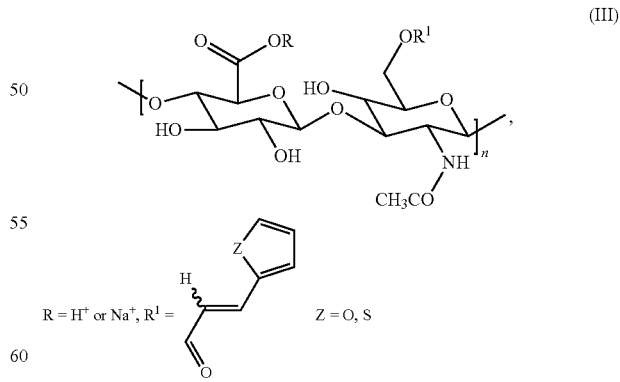

afterwards, the acrylated hyaluronan according to the formula (III) reacts with $C_6$-$C_{18}$-carboxylic acid activated with a chloride of 2,4,6-trichlorobenzoic acid or activated with an organic chloride of R$_3$—CO—Cl, wherein R$_3$ is an aliphatic or branched $C_1$-$C_{30}$-alkyl, under the presence of a base and a catalyst in a mixture of water and a water-miscible aprotic solvent to form $C_6$-$C_{18}$-acylated hyaluronan according to the formula (II), subsequently a nanomicellar composition is prepared from said hyaluronan according to the formula (II), which composition is then subject to a cross-linking reaction by radical reactions.

18. Method of preparation according to claim 16, characterized in that the cross-linking reaction is catalyzed by a cross-linking agent.

19. Method of preparation according to claim 18, characterized in that the cross-linking agent is ammonium peroxydisulfate.

20. The nanomicellar composition according to claim 8, wherein the pharmaceutically or cosmetically active substances are selected from the group consisting of vitamins, medicines, cytostatics, phytoextracts, phytocomplexes, phytoactive substances, and mixtures thereof.

* * * * *

UNITED STATES PATENT AND TRADEMARK OFFICE
CERTIFICATE OF CORRECTION

| | |
|---|---|
| PATENT NO. | : 9,999,678 B2 |
| APPLICATION NO. | : 14/647626 |
| DATED | : June 19, 2018 |
| INVENTOR(S) | : Daniela Smejkalova et al. |

It is certified that error appears in the above-identified patent and that said Letters Patent is hereby corrected as shown below:

On the Title Page

Column 2,
Abstract Lines 1-2, "method of preparation hydrophobized" should be -- method of preparation of hydrophobized --.

Page 4, Column 2,
Line 20, "modem" should be -- modern --.
Line 23, "an dnon-toxic" should be -- and non-toxic --.

In the Specification

Column 1,
Lines 12-13, "method of preparation hydrophobized" should be -- method of preparation of hydrophobized --.
Line 45, "and" should be -- an --.
Line 64, "literature." should be -- literature, --.

Column 2,
Line 59, "method of preparation alkyl/aryl-succinic" should be -- method of preparation of alkyl/aryl-succinic --.

Column 3,
Line 7, "proves" should be -- proven --.
Line 36, "the provision both a polymeric carrier system" should be -- the provision for a polymeric carrier system --.
Line 41, "it is not possible to a conclusion" should be -- it is not possible to draw a conclusion --.

Signed and Sealed this
Thirteenth Day of November, 2018

Andrei Iancu
*Director of the United States Patent and Trademark Office*

CERTIFICATE OF CORRECTION (continued)
U.S. Pat. No. 9,999,678 B2

Column 4,
Line 4, "wherein, however, non-aqueous conditions." should be -- wherein, however, non-aqueous conditions exist. --.
Line 29, "give rise cytotoxic degradation products" should be -- give rise to cytotoxic degradation products --.

Column 5,
Line 1, "claim" should be -- claims --.
Lines 14-15, "due its degradation" should be -- due to its degradation --.
Line 31, "esterification. however," should be -- esterification, however, --.

Column 6,
Line 63, "that that" should be -- than that --.

Column 7,
Line 7, "based on the most of other known polymers," should be -- based on most other known polymers, --.
Line 30, "and" should be -- an --.
Line 55, "solvents" should be -- solvent --.

Column 8,
Line 36, "may benzine" should be -- may be benzine --.

Column 9,
Line 22, "enanthic. caprylic, capric, palmitic, steric." should be -- enanthic, caprylic, capric, palmitic, steric, --.
Line 25, "equivalents. relative" should be -- equivalents, relative --.
Line 46, "acid. one" should be -- acid, one --.

Column 10,
Line 28, "isopropanol. and" should be -- isopropanol, and --.

Column 11,
Lines 46-47, "an chloride" should be -- a chloride --.
Line 53, "method of preparation $C_6$-$C_{18}$-acylated" should be -- method of preparation of $C_6$-$C_{18}$-acylated --.

Column 13,
Line 64, "2,4,6-Trichlorohenzoic Acid" should be -- 2,4,6-Trichlorobenzoic Acid --.

Column 16,
Lines 66-67, "were dissolved" should be -- was dissolved --.

Column 17,
Lines 31-32, "were dissolved" should be -- was dissolved --.
Lines 66-67, "were dissolved" should be -- was dissolved --.

CERTIFICATE OF CORRECTION (continued)
U.S. Pat. No. 9,999,678 B2

Column 18,
Lines 32-33, "were dissolved" should be -- was dissolved --.
Lines 66-67, "were dissolved" should be -- was dissolved --.

Column 19,
Lines 33-34, "were dissolved" should be -- was dissolved --.
Lines 66-67, "were dissolved" should be -- was dissolved --.

Column 20,
Lines 37-38, "were dissolved" should be -- was dissolved --.

Column 21,
Lines 5-6, "were dissolved" should be -- was dissolved --.
Lines 44-45, "were dissolved" should be -- was dissolved --.

Column 22,
Line 56, "Example 1." should be -- Example 1, --.

Column 24,
Line 28, "resulting, solution" should be -- resulting solution --.

Column 26,
Lines 14-15, "am Al plate" should be -- an Al plate --.

Column 27,
Line 42, "was the compared" should be -- was then compared --.
Line 60, "which is as substance" should be -- which is a substance --.

Column 28,
Line 1, "of an substance" should be -- of a substance --.

Column 30,
Line 18, "having been taken." should be -- having been taken, --.

In the Claims

Column 30,
Line 48 (Claim 1), "H+" should be -- $H^+$ --.
Line 50 (Claim 1), "CxHy" should be -- $C_xH_y$ --.
Line 61 (Claim 1), "bounded" should be -- bound --.

CERTIFICATE OF CORRECTION (continued)

Column 32,
Line 8, Formula II in Claim 16. Replace Formula II with the following:

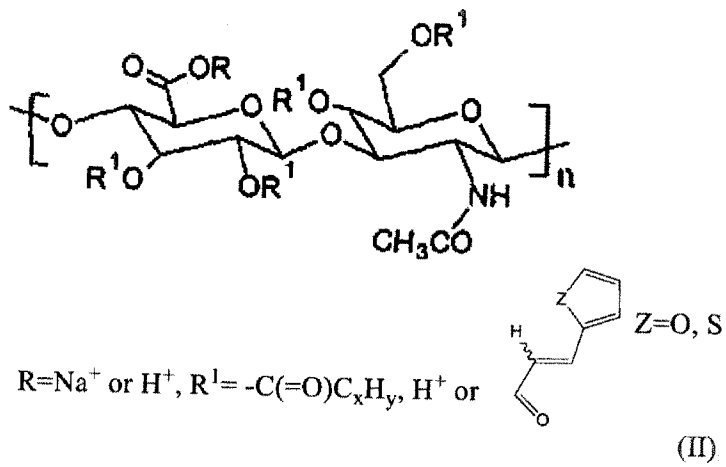

$R=Na^+$ or $H^+$, $R^1= -C(=O)C_xH_y$, $H^+$ or (II)

Line 48, Formula III in Claim 17. Replace Formula III with the following:

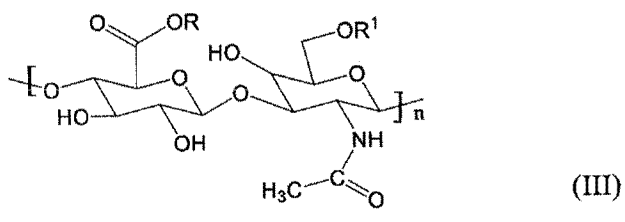

(III)

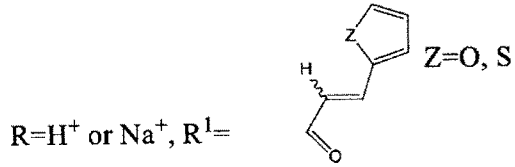

$R=H^+$ or $Na^+$, $R^1=$